(12) United States Patent
Dhanoa et al.

(10) Patent No.: US 7,576,211 B2
(45) Date of Patent: Aug. 18, 2009

(54) SYNTHESIS OF THIENOPYRIDINONE COMPOUNDS AND RELATED INTERMEDIATES

(75) Inventors: Dale S. Dhanoa, Delmar, CA (US); Oren Becker, Mevaseret Zion (IL); Silvia Noiman, Herzliyya (IL); Dongli Chen, Brighton, MA (US); Yael Marantz, Kfar Shmuel (IL); Sharon Shacham, Chestnut Hill, MA (US); Alexander Heifetz, Bnei-Brak (IL); Boaz Inbal, Kfar Shmuel (IL); Shay Bar-Haim, Netanya (IL); Pradyumna Mohanty, Woburn, MA (US); Mercedes Lobera, Concord, MA (US); Laurence Wu, Woburn, MA (US)

(73) Assignee: Epix Delaware, Inc., Lexington, MA (US)

( * ) Notice: Subject to any disclaimer, the term of this patent is extended or adjusted under 35 U.S.C. 154(b) by 0 days.

(21) Appl. No.: 11/269,042

(22) Filed: Nov. 8, 2005

(65) Prior Publication Data

US 2006/0084805 A1    Apr. 20, 2006

Related U.S. Application Data

(63) Continuation of application No. 10/955,434, filed on Sep. 30, 2004, now Pat. No. 7,488,736.

(51) Int. Cl.
*C07D 495/04* (2006.01)
(52) U.S. Cl. ..................................................... 546/114
(58) Field of Classification Search .................. 546/114
See application file for complete search history.

(56) References Cited

U.S. PATENT DOCUMENTS

| | | | |
|---|---|---|---|
| 3,069,412 A * | 12/1962 | Melville et al. .............. 548/953 |
| 3,658,807 A | 4/1972 | Schmidt et al. | |
| 4,146,716 A | 3/1979 | Cox et al. | |
| 4,316,020 A * | 2/1982 | Reissenweber .............. 544/94 |
| 5,155,155 A | 10/1992 | Jurlaro et al. | |
| 5,219,864 A | 6/1993 | Suzuki et al. | |
| 5,227,387 A | 7/1993 | Dreikorn et al. | |
| 5,236,917 A | 8/1993 | Dunlap et al. | |
| 5,371,074 A | 12/1994 | Dunlap et al. | |
| 5,378,679 A | 1/1995 | Nuebling et al. | |
| 5,571,815 A | 11/1996 | Schaper et al. | |
| 5,591,751 A | 1/1997 | Fujioka et al. | |
| 5,593,943 A | 1/1997 | Nuebling et al. | |
| 5,596,012 A | 1/1997 | Dunlap et al. | |
| 5,650,422 A | 7/1997 | Dunlap et al. | |
| 5,753,673 A | 5/1998 | Ohuchi et al. | |
| 5,798,451 A | 8/1998 | von Deyn et al. | |
| 5,874,432 A | 2/1999 | Dunlap et al. | |
| 5,972,841 A | 10/1999 | von Deyn et al. | |
| 6,103,903 A | 8/2000 | Cai et al. | |
| 6,159,962 A | 12/2000 | Steiner et al. | |
| 6,187,788 B1 | 2/2001 | Furuya et al. | |
| 6,222,034 B1 | 4/2001 | Steiner et al. | |
| 6,232,320 B1 | 5/2001 | Stewart et al. | |
| 6,300,333 B1 | 10/2001 | Schaper et al. | |
| 6,340,759 B1 | 1/2002 | Ueno et al. | |
| 6,596,727 B1 | 7/2003 | Schaper et al. | |
| 6,924,283 B2 | 8/2005 | Thorarensen | |
| 7,030,240 B2 | 4/2006 | Dhanoa et al. | |
| 7,119,205 B2 | 10/2006 | Iyengar et al. | |
| 7,153,858 B2 | 12/2006 | Dhanoa et al. | |
| 2002/0028782 A1 | 3/2002 | Castelhano et al. | |
| 2004/0138238 A1 | 7/2004 | Dhanoa et al. | |
| 2005/0049243 A1 | 3/2005 | Ballard et al. | |
| 2005/0065176 A1 | 3/2005 | Field et al. | |
| 2005/0137142 A1 | 6/2005 | Schulz et al. | |
| 2005/0222175 A1 | 10/2005 | Dhanoa et al. | |
| 2005/0222176 A1 | 10/2005 | Dhanoa et al. | |
| 2005/0256153 A1 | 11/2005 | Dhanoa et al. | |
| 2006/0079547 A1 | 4/2006 | Dhanoa et al. | |
| 2006/0084805 A1 | 4/2006 | Dhanoa et al. | |
| 2006/0084806 A1 | 4/2006 | Sridharan et al. | |
| 2006/0205737 A1 | 9/2006 | Becker et al. | |

(Continued)

FOREIGN PATENT DOCUMENTS

EP    0447891 A1    9/1991

(Continued)

OTHER PUBLICATIONS

Jerry March Advanced Organic Chemistry 4th Edition 1992 by John Wiley & Sons: New York pp. 378-383.*

(Continued)

*Primary Examiner*—Rita J Desai
*Assistant Examiner*—David K O'Dell
(74) *Attorney, Agent, or Firm*—Goodwin Procter LLP

(57) ABSTRACT

The invention relates to 5-HT receptor agonists and partial agonists. Novel thienopyridinone compounds represented by Formula I, and synthesis and uses thereof for treating diseases mediated directly or indirectly by 5-HT receptors, are disclosed. Such conditions include Alzheimer's disease, cognition disorders, irritable bowel syndrome, nausea, emesis, vomiting, prokinesia, gastroesophageal reflux disease, non-ulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression. Methods of preparation and novel intermediates and pharmaceutical salts thereof are also included.

2 Claims, No Drawings

U.S. PATENT DOCUMENTS

| | | |
|---|---|---|
| 2006/0234998 A1 | 10/2006 | Dhanoa et al. |
| 2007/0004742 A1 | 1/2007 | Dhanoa et al. |
| 2007/0173487 A1 | 7/2007 | Saha et al. |

FOREIGN PATENT DOCUMENTS

| | | |
|---|---|---|
| EP | 0503844 A | 9/1992 |
| EP | 0505058 A | 9/1992 |
| EP | 0 710 662 A1 | 5/1998 |
| EP | 1 018 513 A2 | 7/2000 |
| EP | 1 018 513 A3 | 7/2000 |
| EP | 0 710 662 B1 | 4/2001 |
| EP | 1229025 | 8/2002 |
| EP | 1325921 A | 7/2003 |
| EP | 1 018 513 B1 | 2/2006 |
| GB | 2295387 | 5/1996 |
| JP | 11 130777 A | 5/1999 |
| WO | WO 94/12176 | 6/1994 |
| WO | WO 94/22871 | 10/1994 |
| WO | WO2005/121151 A | 12/1995 |
| WO | WO-00/64441 A | 11/2000 |
| WO | WO 01/14333 | 3/2001 |
| WO | WO 01/25218 | 4/2001 |
| WO | WO 02/102797 | 12/2002 |
| WO | WO 2004/014850 | 2/2004 |
| WO | WO 2004/017950 | 3/2004 |
| WO | WO 2004/030629 | 4/2004 |
| WO | WO 2004/034963 | 4/2004 |
| WO | WO 2004/089312 | 10/2004 |
| WO | WO 2006/041985 | 4/2006 |
| WO | WO 2007/058805 | 5/2007 |

OTHER PUBLICATIONS

Hwang, Ki-Jun; Lee, Tae-Suk; Kim, Ki-Won; Kim, Beom-Tae; Lee, Chul-Min; Park, Eun-Young; Woo, Ran-Sook. "4-Hydroxy-6-oxo-6,7-dihydro-thieno[2,3-b]pyridine derivatives: synthesis and their biological evaluation for the glycine site acting on the N-methyl-D-aspartate (NMDA) receptor" Archives of Pharmacal Research 2001, 24(4), 270-275.*
Hutchins, R.O. et. al. J. Org. Chem. 1977, 42, 82-91.*
Barker, John M.; Huddleston, Patrick R.; Holmes, David "Thienopyridines. Part 6. Synthesis and nucleophilic substitution of some chlorothieno[2,3-b]pyridine derivatives, and comparisons with the analogous quinoline compounds" Journal of Chemical Research, Synopses 1985 (7), 214-15.*
Gordon W. Gribble "Sodium borohydride in carboxylic acid media: a phenomenal reduction system" Chemical Society Reviews, 1998, 27 395-40.*
Takashi Tojo, Glen W. Spears, Kiyoshi Tsuji, Hiroaki Nishimura, Takashi Ogino, Nobuo Seki Aiko Sugiyama and Masaaki Matsuo "Quinoline-3-carbothioamides and Related Compounds as Novel Immunomodulating Agents" Bioorganic & Medicinal Chemistry Letters 2002 12 2427-2430.*
Coppola et. al. Journal of Organic Chemistry 41 (5), 1976, 825-831.*
Lamlrault, L. et al., "Combined Treatment with Galanthaminium Bromide, a New Chollnesterase Inhibitor, and RS 67333, a Partial Agonist of 5-HT4 Receptors, Enhances Place and Object Recognition In Young Adult and Old Rats." Progress in Neuro-Psychopharmacology & Biological Psychiatry 27 (2003) 185-195.
Moser, Paul C., et al., "SL65.0155, A Novel 5-Hydroxytryplamine4 Receptor Partial Agonist with Potent Cognition-Enhancing Properties," The Journal of Pharmacology and Experimental Therapeutics, 302:731-741, 2002.
Science IP Search, Apr. 30, 2004.
Science IP Search, May 11, 2004.
Stachel, Hans-Dietrich, et al., "Derivatives of Oxalyldimalonic Acid," 1995.
Suzuki, M., "Synthesis and Evaluation of Novel 2-Oxo-1,2-dihydro-3-Quinollnecarboxamide Derivatives as Potent and Selective Serotonin 5-HT4 Receprot Agonists," Chem Pharm. Bull., 49(1) 29-39, 2001.
Buchheit et al. J. Med. Chem., 38(13):2326-2330 (1995).
Buchheit et al. J. Med. Chem., 38(13):2331-2338 (1995).
Kaumann, A.J. Naunyn-Schmiedeberg's Arch. Pharmacol., 342:619-622 (1990).
Abenhaim et al., N. Engl. J. Med, 335(9):609-616 (1996).
Bonhaus, D.W., et al., British J. Pharmac., 1999 (127) 1075-1082.
Brea et al., J. Med. Chem., 45:54-71 (2002).
International Search Report for PCT/US2003/23539 mailed Jul. 23, 2004.
Doggrell, Sheila A., Expert Opin. Investig. Drugs, 2003 (12) 805-823.
Farber et al., N. Engl. J. Med., 351(16):1655-1665 (2004).
Fishman, Chest, 114(3):242S-247S (1998).
Fitzgerald et al., Mol. Pharmacol., 57:75-81 (2000).
Kennett et al., Neuropharmacol., 36(2):233-239 (1997).
Kursar et al., Mol. Pharmacol., 46(2):227-234 (1994).
Kuryshev et al., J. Pharmacol. Exp. Ther., 295(2):614-620 (2000).
Launay et al., Nat. Med., 8(10):1129-1135 (2002).
MacLean, Trends Pharmacol. Sci., 20(12):490-495 (1999).
Manivet et al., J. Biol. Chem., 277(19):17170-17178 (2002).
Marcos et al., Circ. Res., 94:1263-1270 (2004).
Nauser et al., Am. Fam. Physician, 63(9):1789-1798 (2001).
Nebigil et al., Proc. Natl. Acad. Sci. U.S.A., 97(6):2591-2596 (2000).
Poissonnet et al., Mini-Rev. Med. Chem., 4(3):325-330 (2004).
Recanatini, M., et al., Acetylcholinesterase Inhibitors in the Context of Therapeutic Strategies to Combat Alzheimer's Disease, Expert Opinion on Therapeutic Patents, Ashley Publications, GB, vol. 12, No. 12, 2002, pp. 1853-1865.
Rich et al., Chest, 117(3):870-874 (2000).
Roth, B. L., et al., Expert Opin. Ther. Targets, 2001 (5) 685-695.
Rothman et al., Circulation, 102:2836-2841 (2000).
Setola et al., Mol. Pharmacol., 63(6):1223-1229 (2003).
Teoh et al., "Hypoxia Enhances 5-$HT_{2B}$ Receptor Response and Expression in the Rat Pulmonary Artery", Abstract only, International Conference of the American Thoracic Society, San Diego (May 24, 2005).
Ullmer et al., Br. J. Pharmacol., 117(6):1081-1088 (1996).
Ullmer et al., FEBS Lett., 370(3):215-221 (1995).
Witchel et al., J. Clin. Psychopharmacol., 23(1):58-77 (2003).
Witchel et al., FEBS Lett., 512(1-3):59-66 (2002).
Yamada et al., Eur. J. Pharmacol., 406(1):153-157 (2000).
Database Caplus on STN, Accession No. 2000:806616 Horvath, et al., Neurogen Corporation. 6,147,085, Nov. 14, 2000(14.11.2000).

* cited by examiner

SYNTHESIS OF THIENOPYRIDINONE COMPOUNDS AND RELATED INTERMEDIATES

RELATED APPLICATIONS

This application is a continuation of U.S. application Ser. No. 10/955,434 filed Sep. 30, 2004, now U.S. Pat. No. 7,488,736, which is incorporated by reference herein in its entirety. This application is also related to co-pending application Ser. No. 10/960,769 filed Oct. 7, 2004, which is hereby incorporated herein in its entirety.

FIELD OF THE INVENTION

The invention generally relates to the field of serotonin (5-hydroxytryptamine, or 5-HT) receptor modulators, e.g., agonists, partial agonists, inverse agonists, antagonists, and more particularly to new thienopyridinone compounds, the synthesis and use of these compounds and their pharmaceutical compositions, e.g., in the treatment, modulation and/or prevention of physiological conditions associated with serotonin action, such as in treating Alzheimer's disease, cognition disorders, irritable bowel syndrome, nausea, emesis, vomiting, prokinesia, gastroesophageal reflux disease, non-ulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

BACKGROUND OF THE INVENTION

The serotonergic neural system of the brain has been shown to influence a variety of physiologic functions which manifest themselves in a variety of disorders such as Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

5-HT receptor modulators e.g., agonists, partial agonists, inverse agonists and antagonists, and/or selective serotonin reuptake inhibitors (SSRIs) such as fluoxetine, paroxetine, fluvoxamine, sertraline, lorazepam, imipramine, citalopram, and nortriptyline, may be used for the treatment of the above conditions, as well as for vasodilation, smooth muscle contraction, bronchoconstriction, brain disorders such as vascular disorders such as angina and migraine; and neuropathological disorders including Parkinson's disease and Alzheimer's disease. They also intervene in the regulation of the cerebral circulation and thus represent effective agents for controlling migraine. They are also suitable for the prophylaxis and control of the effects of occurrences of cerebral infarct (Apoplexia cerebri) such as stroke or cerebral ischemia. They are also suitable for the control of disorders of the intestinal tract which are characterized by disturbances of the serotoninergic system and also by disturbances of the carbohydrate metabolism. They are suitable for the treatment of gastrointestinal disorders including irritable bowel syndrome.

Trazodone controls 5-HT actions, and fluoxetine and fluvoxamine facilitate serotonergic neurotransmission via potent and selective inhibition of serotonin reuptake into presynaptic neurons. 3-Chloroimipramine inhibits both 5-HT and norepinephrine reuptake. Other compounds of current interest as antidepressants include zimeldine, bupropion and nomifensine.

Tegaserod, an indazole carbazimidamide that acts as a $5\text{-HT}_4$ agonist, has been approved for irritable bowel syndrome (Buchheit et al. *J. Med. Chem.* 1995, 38, 2331-2338; Buchheit et. al., *J. Med. Chem.* 1995, 38, 2326-2330).

The $5\text{-HT}_4$ receptors represent a member of the family of receptors with seven transmembrane (7TM) domains coupled to a G-protein which is positively coupled to adenylate cyclase. The $5\text{-HT}_4$ receptors are expressed in a wide variety of tissues, including the human brain and the rodent brain, the human, dog, pig and rodent gastro-intestinal tract, and the pig and human heart. In the mammalian brain, the $5\text{-HT}_4$ receptors contribute to dopamine secretion and regulate learning and long-term memory via the modification of acetylcholine release. In the peripheral tissues, the $5\text{-HT}_4$ receptors have proven to regulate gastro-intestinal tract motility, intestinal electrolyte secretion, adrenal secretion of corticosteroids, bladder contraction and atrium contractility.

The $5\text{-HT}_4$ receptors are involved in a wide variety of central and peripheral disorders, including cardiac arrhythmias and neurodegenerative disorders and more specifically Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

The development of $5\text{-HT}_4$ receptor modulators, e.g., agonists, partial agonists, inverse agonists and antagonists, may have therapeutic applications in the central nervous system for treating neuropsychiatric disorders associated with a dysfunction of the central dopaminergic system, such as Parkinson's disease, or for treating amnesic deficiencies as presented in patients suffering from Alzheimer's disease. Such medicines might also be useful for treating peripheral disorders such as irritable bowel syndrome, gastroparesis, urinary incontinence and cardiac arrhythmias. Selective, high affinity, metabolically stable $5\text{-HT}_4$ receptor modulators that possess good bioavailability, CNS penetration, and good pharmacokinetic properties, e.g., in vivo, are desirable.

SUMMARY OF THE INVENTION

The present invention relates to the discovery of new compounds which are $5\text{-HT}_4$ modulators, e.g., agonists, partial agonists, inverse agonists and antagonists, and/or SSRIs, that can be used for treating, preventing or curing 5-HT-related conditions, such as Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

In particular, it has been found that certain thienopyridinone compounds are effective $5\text{-HT}_4$ receptor partial agonists and/or full agonists and act as antagonists and/or SSRIs. In an embodiment, such compounds include those having the formula

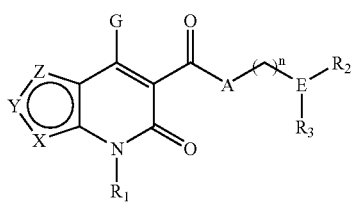

(I)

wherein $R_1$ may be $(C_1-C_8)$ branched or unbranched alkyl or alkenyl (e.g., isopropenyl); a $(C_1-C_8)$ substituted or unsubstituted carbocyclic ring; a substituted or unsubstituted aryl or heteroaryl ring, branched or unbranched haloalkyl (e.g., $CF_3$, $CF_3-CH_2$, $CF_3-CF_2-$); or a substituted or unsubstituted $(CH_2)_p$-aryl, $(CH_2)_p$-heteroaryl ring, where p is 1, 2, 3, or 4;

$R_2$ and $R_3$ may independently be H; $(C_1-C_6)$ branched or unbranched alkyl; a $(C_1-C_6)$ substituted or unsubstituted carbocyclic ring; substituted or unsubstituted $(C_1-C_6)$alkylhydroxy, substituted or unsubstituted $(C_1-C_6)$alkylalkoxy, substituted or unsubstituted $(C_1-C_6)$ alkylamino, substituted or unsubstituted $(C_1-C_6)$alkylaminoacyl, or substituted or unsubstituted $(C_1-C_6)$alkylaminoaryl; or, when taken together, $R_2$ and $R_3$ form a substituted or unsubstituted piperidine (N-containing six-membered cyclic ring), pyrrolidine (N-containing five membered cyclic ring), azepane (N-containing seven-membered cyclic ring), aziridine (N-containing three-membered ring), or azetidine (N-containing four-membered cyclic ring);

X, Y, Z may independently be S, C, N, or O;

A may be NH, $N(C_1-C_6)$ alkyl or a $N(C_1-C_6)$carbocyclic ring; $CH_2$; CH(alkyl); or O;

E may be N, CH, O, N—CO—, or N—$(CO)_2$—;

G may be H; OH; branched or unbranched $(C_1-C_6)$alkyl; branched or unbranched O—$(C_1-C_6)$ alkyl; a substituted or unsubstituted $(C_1-C_6)$carbocyclic ring; branched or unbranched O—C(O)—$(C_1-C_6)$alkyl; a substituted or unsubstituted O—CO—$(C_1-C_6)$carbocyclic ring; $NH_2$, branched or unbranched $NH(C_1-C_6)$alkyl; a substituted or unsubstituted $NH(C_1-C_6)$carbocyclic ring; $N[(C_1-C_6)alkyl]_2$, substituted or unsubstituted $N[(C_1-C_6)carbocyclic]_2$; branched or unbranched NH—C(O)—$(C_1-C_6)$alkyl; a substituted or unsubstituted NH—CO—$(C_1-C_6)$carbocyclic ring, branched or unbranched NH—C(O)—O—$(C_1-C_6)$alkyl; or a substituted or unsubstituted NH—CO—$(C_1-C_6)$—O-carbocyclic ring;

and n may be 1, 2, 3, 4, 5 or 6;

and pharmaceutically acceptable salts thereof.

In an embodiment, E may be N, and $R_2$ and $R_3$, taken together, may form a five (pyrrolidine) or six membered ring (piperidine).

E may be N, X may be S, Y may be CH, Z may be CH, $R_1$ may be methyl, ethyl, n-propyl, isopropyl, n-butyl, isobutyl, sec-butyl, $CF_3$, $CH_2CF_3$, $CH(CF_3)_2$, or $CH_2CF_3$; G may be OH, A may be NH, $CH_2$, or 0, and n may be 1, 2 or 3.

In another embodiment, $R_1$ is a methyl, ethyl, isopropyl, n-propyl, allyl, n-butyl or isobutyl; $R_2$ and $R_3$ taken together form a substituted or unsubstituted piperidine or pyrrolidine ring; X is S; Y and Z are C; A is NH, $CH_2$, or O; E is N; G is OH; and n is 1, 2, 3, or 4. In another embodiment, $R_1$ is methyl, ethyl, isopropyl, n-propyl, allyl, n-butyl or isobutyl; $R_2$ and $R_3$ taken together form a substituted or unsubstituted piperidine (N-containing six-membered cyclic ring), pyrrolidine (N-containing five membered cyclic ring), or azepane (N-containing seven-membered cyclic ring); X is S; Y and Z are C; A is NH; G is OH; and n is 3. In another embodiment, $R_1$ is isopropyl; $R_2$ and $R_3$ taken together form a substituted or unsubstituted piperidine (N-containing six-membered cyclic ring); X is S; Y and Z are C; A is NH; G is OH; and n is 3.

In another embodiment, compounds of the invention include those having the formula

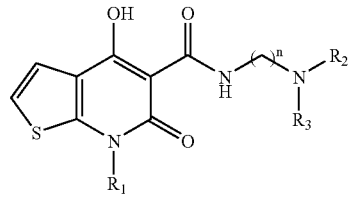

(II)

wherein $R_1$ may be $(C_1-C_8)$ branched or unbranched alkyl or alkenyl; a $(C_1-C_8)$ substituted or unsubstituted carbocyclic ring; a substituted or unsubstituted aryl or heteroaryl ring; branched or unbranched haloalkyl (e.g., $CF_3$, $CF_3-CH_2$, $CF_3-CF_2-$); or a substituted or unsubstituted $(CH_2)_p$-aryl or $(CH_2)_p$-heteroaryl ring, where p is 1, 2, 3, or 4;

$R_2$ and $R_3$, taken together, form a substituted or unsubstituted piperidine (N-containing six-membered cyclic ring), pyrrolidine (N-containing five membered cyclic ring), azepane (N-containing seven-membered cyclic ring), aziridine (N-containing three-membered ring), or azetidine (N-containing four-membered cyclic ring); and n may be 1, 2, 3, 4, 5 or 6; and pharmaceutically acceptable salts thereof.

Compounds of the invention may also be 5-HT receptor modulators, e.g., 5-$HT_4$ receptor agonists, partial agonists, inverse agonists and/or antagonists.

In another embodiment compounds of the invention may also be 5-HT receptor agonists, e.g., 5-$HT_4$ receptor agonists.

In another embodiment compounds of the invention may also be 5-HT receptor partial agonists, e.g., 5-$HT_4$ receptor partial agonists.

In another embodiment compounds of the invention may also be 5-HT receptor inverse agonists, e.g., 5-$HT_4$ receptor inverse agonists.

In another embodiment compounds of the invention may also be 5-HT receptor antagonists, e.g., 5-$HT_4$ receptor antagonists.

Another aspect of the invention is a pharmaceutical composition comprising an amount of a compound according to Formula I effective to treat diseases such as Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, or respiratory depression, and a pharmaceutically acceptable carrier.

Another aspect of the invention is a method for treating diseases such as Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, or respiratory depression in a mammal such as a human comprising administering a therapeutically effective amount of a compound according to Formula I.

Another aspect of the invention is a pharmaceutical composition comprising an amount of a compound according to Formula I effective to treat Alzheimer's Disease in a mammal suffering therefrom, and a pharmaceutically acceptable carrier.

Another aspect of the invention is a method for treating Alzheimer's Disease in a mammal such as a human comprising administering a therapeutically effective amount of a compound according to Formula I.

Another aspect of the invention is a pharmaceutical composition comprising an amount of a compound according to Formula I effective for memory enhancement in a mammal in need thereof, and a pharmaceutically acceptable carrier.

Another aspect of the invention is a method for memory enhancement in a mammal such as a human comprising administering a therapeutically effective amount of a compound according to Formula I.

Another aspect of the invention is a pharmaceutical composition comprising an amount of a compound according to Formula I effective in treating irritable bowel syndrome (IBS); and a pharmaceutically acceptable carrier.

Another aspect of the invention is a method of treating irritable bowel syndrome (IBS) comprising administering a therapeutically effective amount of a compound according to Formula I.

Processes for preparing the compounds and novel intermediates are also included in the invention.

DETAILED DESCRIPTION OF THE INVENTION

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

Definitions

For convenience, certain terms used in the specification, examples, and appended claims are collected here.

"5-HT receptor modulator" or "5-HT modulator" includes compounds having effect at the $5\text{-}HT_1$, $5\text{-}HT_2$, $5\text{-}HT_3$, $5\text{-}HT_4$, $5\text{-}HT_5$, $5\text{-}HT_6$ or $5\text{-}HT_7$ receptors, including the subtypes of each receptor type, such as $5\text{-}HT_{1A, B, C, D, E \text{ or } F}$; $5\text{-}HT_{2A, B \text{ or } C}$; $h5HT_{4a, b, c, d \text{ or } e}$; and $5\text{-}HT_{5A \text{ or } B}$. 5-HT modulators may be agonists, partial agonists, inverse agonists, or antagonists.

"Treating", includes any effect, e.g., lessening, reducing, modulating, or eliminating, that results in the improvement of the condition, disease, disorder, etc.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups which have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1\text{-}C_6$ for straight chain, $C_3\text{-}C_6$ for branched chain), and more preferably four or fewer. Likewise, preferred cycloalkyls have from three to eight carbon atoms in their ring structure, and more preferably have five or six carbons in the ring structure. "$C_1\text{-}C_6$" includes alkyl groups containing one to six carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Combination therapy" (or "co-therapy") includes the administration of a 5-HT modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

Compounds of the invention may generally be used in the treatment or prophylaxis of gastrointestinal disorders, cardiovascular disorders and CNS disorders. They are of potential interest in the treatment of irritable bowel syndrome (IBS), in particular the diarrhea aspects of IBS, i.e., these compounds block the ability of 5-HT to stimulate gut motility via activation of enteric neurons. In animal models of IBS, this can be conveniently measured as a reduction of the rate of defecation. They are also of potential use in the treatment of urinary incontinence which is often associated with IBS. They may also be of potential use in other gastrointestinal disorders, such as those associated with upper gut motility, and as anti-emetics. In particular, they are of potential use in the treatment of the nausea and gastric symptoms of gastro-esophageal reflux disease and dyspepsia. Anti-emetic activity is determined in known animal models of cytotoxic-agent/radiation induced emesis.

Specific cardiac 5-$HT_4$ receptor antagonists which prevent atrial fibrillation and other atrial arrhythmias associated with 5-HT, would also be expected to reduce occurrence of stroke (see A. J. Kaumann 1990, *Naumyn-Schmiedeberg's Arch. Pharmacol.* 342, 619-622, for appropriate animal test method).

The invention thus further provides a method of treatment of irritable bowel syndrome, gastro-esophageal reflux disease, dyspepsia, atrial arrhythmias, stroke and ischemic stroke, anxiety, migraine, Alzheimer's disease, cognition disorders, nausea, emesis, vomiting, prokinesia, gastroesophageal reflux disease, nonulcer dyspepsia, depression, anxiety, urinary incontinence, atrial fibrillation, gastritis, gastric emptying disorders, feeding disorders, gastrointestinal disorders, constipation, erectile dysfunction and/or respiratory depression in mammals, such as humans, which comprises the administration of an effective amount of a compound of the formula (I) or a pharmaceutically acceptable salt thereof. In particular, the method comprises treatment of IBS or atrial arrhythmias and stroke.

The compounds of the invention have a high affinity and specificity for 5-$HT_4$ serotoninergic receptors. They are able to stimulate or inhibit, either at central or peripheral level, those effects mediated by the activation of this receptor subtype. Therefore, the compounds of the invention may be defined as novel agonists or partial agonists, antagonists or inverse agonists in vitro and in vivo of 5-$HT_4$ receptors. 5-$HT_4$ receptors belong to the family of serotoninergic receptors and they are among those more recently discovered, pharmacologically characterized and cloned. After the first identification in discrete areas of guinea-pig CNS, the 5-$HT_4$ serotoninergic receptors have been localized also in other districts, either central or peripheral (ileum, atrium, esophagus, colon, urinary bladder and adrenal glands) of different species, including humans. The presence of these receptors in different organs and tissues, make it possible that compounds able to block the effects of their hyperstimulation, may be advantageously used in the treatment and in the prophylaxis of different pathological situations.

Thus, for example, since the stimulation of 5-$HT_4$ atrial cardiac receptors, besides causing inotropic and chronotropic positive effects, is responsible for arrhythmias observed in some experimental conditions, antagonists to these receptors may be used in the specific treatment of cardiac rhythm disorders, such as atrial fibrillation and other types of arrhythmias. In the gastro-intestinal tract, since the 5-$HT_4$ receptors mediate the prokinetic and secretory action of serotonin, it can be suggested the use of 5-$HT_4$ antagonists in the treatment of disorders connected to an altered intestinal motility or secretion such as IBS, more particularly in those forms of IBS combined to diarrheic states. The presence of 5-$HT_4$ receptors in the central nervous system of either rat or humans may be limited to defined areas such as hippocampus, frontal cortex, basal ganglia and limbic structures. Compounds able to control an altered stimulation of the 5-$HT_4$ receptors in the CNS may therefore be used in the psychiatric and neurological fields such as Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, or respiratory depression. Moreover, since it has been described that 5-$HT_4$ receptors partially mediate the effect of 5-HT in controlling ethanol intake, 5-$HT_4$ antagonists might be useful in the treatment of alcohol abuse. 5-$HT_4$ receptors are also involved in the control of other functions of the genitourinary and adrenal glands system, where they seem to mediate the release of steroidal hormones. Consequently, pathologies characterized by an altered secretion of hormones or urinary incontinence might be also treated with compounds able to block the 5-$HT_4$ receptors.

The present invention relates to the discovery of new compounds which are 5-HT modulators, e.g., agonists, partial agonists, antagonists, and/or SSRIs, that can be used for treating, preventing or curing 5-HT-related conditions. In particular, it has been found that certain thienopyridinone compounds are effective 5-HT receptor modulators, more specifically 5-$HT_4$, 5-$HT_{4a}$ and 5-$HT_{4e}$ receptor modulators and/or SSRIs.

In an embodiment, such compounds include those having the formula

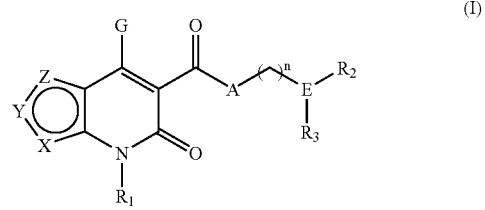

(I)

wherein $R_1$ may be ($C_1$-$C_8$) branched or unbranched alkyl; a ($C_1$-$C_8$) substituted or unsubstituted carbocyclic ring; a substituted or unsubstituted aryl or heteroaryl ring, and a substituted or unsubstituted $(CH_2)_p$-aryl, $(CH_2)_p$-heteroaryl ring, where p is 1, 2, 3, or 4;

$R_2$ and $R_3$ may independently be H; ($C_1$-$C_6$) branched or unbranched alkyl; a ($C_1$-$C_6$) substituted or unsubstituted carbocyclic ring; substituted or unsubstituted ($C_1$-$C_6$)alkylhydroxy, substituted or unsubstituted ($C_1$-$C_6$)alkylalkoxy, substituted or unsubstituted ($C_1$-$C_6$)alkylamino, substituted or unsubstituted ($C_1$-$C_6$)alkylaminoacyl, or substituted or unsubstituted ($C_1$-$C_6$)alkylaminoaryl; or, when taken together, $R_2$ and $R_3$ form a substituted or unsubstituted piperidine (N-containing six-membered cyclic ring), pyrrolidine (N-containing five membered cyclic ring), azepane (N-containing seven-membered cyclic ring), aziridine (N-containing three-membered ring), or azetidine (N-containing four-membered cyclic ring);

X, Y, Z may independently be S, C, N, or O;

A may be NH, N($C_1$-$C_6$)alkyl, or a N($C_1$-$C_6$)carbocyclic ring; $CH_2$; CH(alkyl); or O;

E may be N, CH, O, N—CO—; or N—$(CO)_2$—

G may be H; OH; branched or unbranched ($C_1$-$C_6$)alkyl; branched or unbranched O—($C_1$-$C_6$)alkyl; a substituted or unsubstituted ($C_1$-$C_6$)carbocyclic ring; branched or unbranched O—C(O)—($C_1$-$C_6$)alkyl; a substituted or unsubstituted O—CO—($C_1$-$C_6$)carbocyclic ring; $NH_2$, branched or unbranched NH($C_1$-$C_6$)alkyl; a substituted or unsubstituted NH($C_1$-$C_6$)carbocyclic ring; N[($C_1$-$C_6$)alkyl]$_2$, substituted or unsubstituted N[($C_1$-$C_6$)carbocyclic]$_2$; branched or unbranched NH—C(O)—($C_1$-$C_6$)alkyl; a substituted or unsubstituted NH—CO—($C_1$-$C_6$)carbocyclic ring, branched or unbranched NH—C(O)—O—($C_1$-$C_6$)alkyl; or a substituted or unsubstituted NH—CO—($C_1$-$C_6$)—O-carbocyclic ring; and n may be 1, 2, 3, 4, 5 or 6; and pharmaceutically acceptable salts thereof.

In an embodiment, E may be N, and $R_2$ and $R_3$, taken together, may form a five (pyrrolidine) or six membered ring (piperidine). E may be N, X may be S, Y may be CH, Z may be CH, $R_1$ may be ethyl, isopropyl, propyl, butyl or isobutyl, G may be OH, A may be NH or O, and n may be 1, 2 or 3.

In another embodiment, compounds of the invention include those having the formula

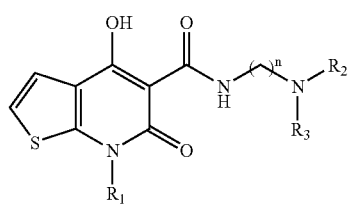

(II)

wherein $R_1$ may be ($C_1$-$C_8$) branched or unbranched alkyl or alkenyl (e.g., isopropenyl); a ($C_1$-$C_8$) substituted or unsubstituted carbocyclic ring; a substituted or unsubstituted aryl or heteroaryl ring, branched or unbranched haloalkyl (e.g., $CF_3$, $CF_3$—$CH_2$, $CF_3$—$CF_2$—); or a substituted or unsubstituted $(CH_2)_p$-aryl, $(CH_2)_p$-heteroaryl ring, where p is 1, 2, 3, or 4;

$R_2$ and $R_3$, taken together, form a substituted or unsubstituted piperidine (N-containing six-membered cyclic ring), pyrrolidine (N-containing five membered cyclic ring), azepane (N-containing seven-membered cyclic ring), aziridine (N-containing three-membered cyclic ring), or azetidine (N-containing four-membered cyclic) ring; and n may be 1, 2, 3, 4, 5 or 6; and pharmaceutically acceptable salts thereof.

Compounds of the invention may also be 5-HT receptor antagonists, e.g., 5-$HT_4$ receptor antagonists.

In another embodiment compounds of the invention may also be 5-HT receptor partial agonists, e.g., 5-$HT_4$, 5-$HT_{4a}$, 5-$HT_{4e}$ receptor partial agonists.

In another embodiment compounds of the invention may also be 5-HT receptor agonists, e.g., 5-$HT_4$ receptor agonists.

In another embodiment compounds of the invention may also be 5-HT receptor inverse agonists, e.g., 5-$HT_4$ receptor inverse agonists.

Another aspect of the invention is a pharmaceutical composition comprising an amount of a compound according to Formula I effective to treat diseases of the central nervous system in a mammal suffering therefrom, and a pharmaceutically acceptable carrier.

Another aspect of the invention is a method for treating diseases of the central nervous system in a mammal such as a human comprising administering a therapeutically effective amount of a compound according to Formula I.

Another aspect of the invention is a pharmaceutical composition comprising an amount of a compound according to Formula I effective to treat Alzheimer's Disease in a mammal suffering therefrom, and a pharmaceutically acceptable carrier.

Another aspect of the invention is a method for treating Alzheimer's Disease in a mammal such as a human comprising administering a therapeutically effective amount of a compound according to Formula I.

Another aspect of the invention is a pharmaceutical composition comprising an amount of a compound according to Formula I effective for memory enhancement in a mammal in need thereof, and a pharmaceutically acceptable carrier.

Another aspect of the invention is a method for memory enhancement in a mammal such as a human comprising administering a therapeutically effective amount of a compound according to Formula I.

Another aspect of the invention is a pharmaceutical composition comprising an amount of a compound according to Formula I effective in treating irritable bowl syndrome (IBS); and a pharmaceutically acceptable carrier.

Another aspect of the invention is a method of treating irritable bowl syndrome (IBS) comprising administering a therapeutically effective amount of a compound according to Formula I.

Processes for preparing the compounds and novel intermediates are also included in the invention.

The compounds of the invention are valuable for treating a wide variety of clinical conditions which are characterized by serotonin excess or absence, e.g., serotonergic hypofunction or hyperfunction. Such conditions include schizophrenia and other psychotic disorders, for example, schizophrenic disorders, schizoaffective disorders, delusional disorders, brief psychotic disorders, shared psychotic disorders and psychotic disorders with delusions or hallucinations; gastrointestinal disorders like Crohn's disease, eating disorders, neuralgia, and addiction disorders; obsessive compulsive disorders, panic disorders, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, e.g., specific animal phobias, social phobias, stress disorders including post-traumatic stress disorder and acute stress disorder, and generalized anxiety disorders; delirium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple etiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral edema.

Compounds of the invention may be used for the treatment of the above conditions, as well as for vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; pulmonary hypertension and systemic hypertension; and neuropathological disorders including Parkinson's disease and Alzheimer's disease; modulation of the cardiovascular system; prophylaxis and control of the effects of occurrences of cerebral infarct (Apoplexia cerebri) such as stroke or cerebral ischemia; and for the control of disorders of the intestinal tract which are characterized by disturbances of the serotoninergic system and also by disturbances of the carbohydrate metabolism.

The compounds may also be useful in treating a variety of other conditions including stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

For treating certain conditions it may be desirable to employ the compounds of the invention in conjunction with another pharmacologically active agent. The compounds of the invention may be presented together with another therapeutic agent as a combined preparation for simultaneous, separate or sequential use. Such combined preparations may be, for example, in the form of a twin pack.

A further aspect of the invention comprises compounds of the invention in combination with a or another 5-HT antagonist and/or SSRI, e.g., a $5-HT_3$ antagonist such as ondansetron, granisetron, tropisetron or zatisetron. Additionally, the compounds of the invention may be administered in combination with an anti-inflammatory corticosteroid, such as dexamethasone. Furthermore, the compounds of the invention may be administered in combination with a chemotherapeutic agent such as an alkylating agent, anti-metabolite, mitotic inhibitor or cytotoxic antibiotic, as described above. In general, the currently available dosage forms of the known therapeutic agents for use in such combinations will be suitable.

According to a further or alternative aspect, the invention provides compounds of the invention for use in the manufacture of a medicament for the treatment or prevention of physiological disorders associated with serotonin excess or absence, e.g., serotonergic hypofunction or hyperfunction.

The invention also provides methods for treating or preventing physiological disorders associated with serotonin excess or absence, e.g., serotonergic hypofunction or hyperfunction, which method comprises administration to a patient in need thereof of an effective amount of a compound of the invention or a composition comprising a compound of the invention.

For treating or preventing migraine, the compounds of the invention may be used in conjunction with other anti-migraine agents, such as ergotamines or $5-HT_1$ agonists, especially sumatriptan or rizatriptan. Likewise, for treating behavioral hyperalgesia, the compounds of the invention may be used in conjunction with an antagonist of N-methyl D-aspartate (NMDA), such as dizocilpine.

It will be further appreciated that for treating or preventing depression and/or anxiety, the compounds of the invention may be used in combination with an antidepressant agent or anti-anxiety agent. Suitable classes of antidepressant agents of use in the invention include: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, β-adrenoreceptor antagonists and atypical antidepressants. Another class of antidepressant agent of use in the invention is noradrenergic and specific serotonergic antidepressants, such as mirtazapine. Suitable examples of norepinephrine reuptake inhibitors include amitripdyline, clomipramine, doxepine, imipramine, trimipramine, amoxapine, desipramine, maprotiline, nortriptyline, reboxetine and protriptyline and pharmaceutically acceptable salts thereof. Suitable examples of selective serotonin reuptake inhibitors include fluoxetine, fluvoxamine, paroxetine, and sertraline and pharmaceutically acceptable salts thereof. Suitable examples of monoamine oxidase inhibitors include isocarboxazid, phenelzine, tranylcypromain and selegiline, and pharmaceutically acceptable salts thereof. Suitable examples of reversible monoamine oxidase inhibitors include moclobemide, and pharmaceutically acceptable salts thereof. Suitable examples of serotonin and noradrenaline reuptake inhibitors include venlafaxine, and pharmaceutically acceptable salts thereof. Suitable examples of corticotropin releasing factor (CRF) antagonists include those compounds described in International Patent Specification Nos. WO 94/13643, WO 94/13644, WO 94/13661, WO 94/13676 and WO 94/13677. Suitable examples of atypical antidepressants include bupropion, lithium, nefazoedone, sibutramine, trazodone and viloxazine, and pharmaceutically acceptable salts thereof. Other antidepressants of use in the invention include adinozolam, alaproclate, amineptine, amitryptyline/chlordiazepoxide combination, atipamezole, azamianserin, bazinaprine, fefuraline, bifemelane, binodaline, bipenamol, brofaromine, bupropion, caroxazone, cericlamine, cianopramine, cimoxatone, citalopram, clemeprol, clovoxamine, dasepinil, deanol, demexiptiline, dibenzepin, dothiepin, droxidopa, enefexine, setazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirindole, pizotyline, ritaserin, rolipram, sercloremine, setiptiline, sibutramine, sulbutiamine, sulpride, teniloxazine, thozalinone, thymoliberin, tianeptine, tiflucarbine, tofenacin, tofisopam, toloxatone, tomoxetine, veralipride, viqualine, zimelidine, and zometapine, and pharmaceutically acceptable salts thereof, and St. John's wort herb, or Hypericum perforatum, or extracts thereof. Preferred antidepressant agents include selective serotonin reuptake inhibitors, in particular, fluoxetine, fluvoxamine, paroxetine, and sertraline and pharmaceutically acceptable salts thereof.

Suitable classes of anti-anxiety agents of use in the invention include benzodiazepines and $5-HT_{1A}$ agonists or antagonists, especially $5-HT_{1A}$ partial agonists, and corticotropin releasing factor (CRF) antagonists. In addition to benzodiazepines, other suitable classes of anti-anxiety agents are non-benzodiazepine sedative-hypnotic drugs such as zolpidem; mood-stabilizing drugs such as clobazam, gabapentin, lamotrigine, loreclezole, oxcarbamazepine, stiripentol and vigabatrin; and barbiturates. Suitable benzodiazepines of use in the invention include alprazolam, chlordizepoxide, clonazepam, chlorazepate, diazepam, halazepam, lorezepam, oxazepam and prazepam, and pharmaceutically acceptable salts thereof. Suitable examples of 5-HT$_{1A}$ agonists or antagonists of use in the invention include, in particular, the 5-HT$_{1A}$ partial agonists buspirone, flesinoxan, gepirone, ipsapirone and pindolol, and pharmaceutically acceptable salts thereof. Another class of anti-anxiety agent of use in the invention are compounds having muscarinic cholinergic activity. Suitable compounds in this class include m1 muscarinic cholinergic receptor antagonists such as those compounds described in European Patent Specification Nos. 0 709 093, 0 709 094 and 0 773 021 and International Patent Specification No. WO 96/12711. Another class of anti-anxiety agent of use in the invention are compounds acting on ion channels. Suitable compounds in this class include carbamazepine, lamotrigine and valproate, and pharmaceutically acceptable salts thereof.

Therefore, in a further aspect of the invention, a pharmaceutical composition is provided comprising a compound of the invention and an antidepressant or an anti-anxiety agent, together with at least one pharmaceutically acceptable carrier or excipient.

Suitable antipsychotic agents of use in combination with the compounds of the invention include phenothiazines, e.g., chlorpromazine, mesoridazine, thioridazine, acetophenazine, fluphenazine, perphenazine and trifluoperazine; thioxanthenes, e.g., chlorprothixene or thiothixene; heterocyclic dibenzazepines, e.g., clozapine or olanzapine; butyrophenones, e.g., haloperidol; diphenylbutylpiperidines, e.g., pimozide; and indolones, e.g., molindolene. Other antipsychotic agents include loxapine, sulpiride and risperidone. It will be appreciated that the antipsychotic agents when used in combination with the compounds of the invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with the compounds of the invention include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with the compounds of the invention is the 5-HT$_{2A}$ receptor antagonists, examples of which include MDL100907 and fananserin. Also of use in combination with the compound of the invention are the serotonin dopamine antagonists (SDAs) which are believed to combine 5-HT$_{2A}$ and dopamine receptor antagonist activity, examples of which include olanzapine and ziperasidone.

Therefore, in a further aspect of the invention, a pharmaceutical composition is provided comprising a compound of the invention and an antipsychotic agent, together with at least one pharmaceutically acceptable carrier or excipient.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with a serotonin excess or absence, e.g., serotonergic hypofunction or hyperfunction, an appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the peptides of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives of the compounds of formula (I) such as the compounds quaternized by compounds $R_x$-T wherein $R_x$ is $C_{1-6}$ alkyl, phenyl-$C_{1-6}$-alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide, e.g., chloride, bromide or iodide. Yet other examples of pharmaceutically acceptable salts also include internal salts such as N-oxides.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Methods for preparing the compounds of this invention are illustrated in the following synthetic schemes and example(s). The following schemes, examples and biological data are given for the purpose of illustrating the invention, but not for limiting the scope or spirit of the invention.

Synthesis Of Novel Thienopyridone Compounds

Novel thienopyridinone compounds of the general structure 1 disclosed herein were synthesized by the coupling reaction between the 3-(piperidin-1-yl)propan-1-amine (2) and the ester (3) as shown below.

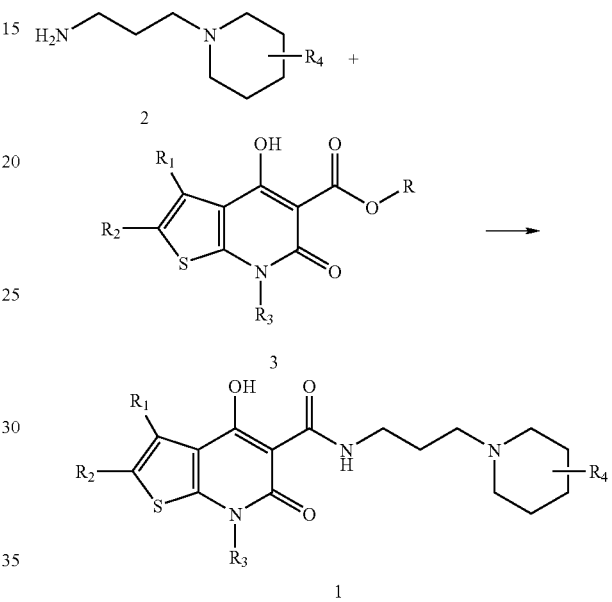

Preparation of substituted or unsubstituted 3-(piperidin-1-yl)propan-1-amine (2) can be accomplished via Step A as shown in Scheme 1. Reaction between N-(3-bromopropyl) phthalimide (4) with substituted or unsubstituted piperidine (5) followed by removal of the phthalimide group by the use of hydrazine hydrate affords 2 in good yield.

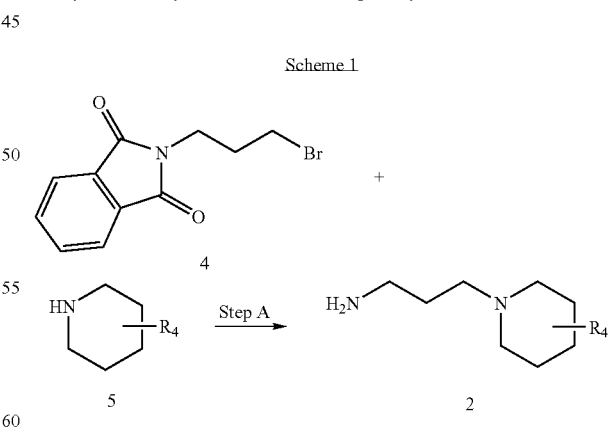

Synthesis of the novel thienopyridinone compounds and their salts are described in Scheme 2. Reductive alkylation of substituted or unsubstituted 2-aminothiophene-3-carboxylate (6) with an aldehyde or a ketone in Step B yielded the alkylated product 7. Hydrolysis of 7 followed by reaction with triphosgene in Step C formed the highly reactive anhydride 8.

Thermal reaction of 8 with diethyl malonate under basic condition in Step D led to the formation of the ester (3, R=Et), which upon heating in the presence of 2 with toluene as solvent in Step E afforded 1 in its free base form. Salt formation of 1 in Step F with inorganic acids (such as hydrochloric acid), organic acids (such as maleic acid, citric acid and succinic acid) or metallic bases (such as sodium hydride and potassium tert-butoxide) provide the respective inorganic acid (hydrochloride), organic acid (maleate, citrate and succinate) or metallic (sodium and potassium) salts.

Preparation of the key intermediate (3, R=Me) can be alternatively accomplished by Step G in Scheme 3. Amide formation of 7 with ethyl 3-chloro-3-oxopropionate and triethylamine followed by intramolecular condensation reaction in the presence of sodium methoxide effected the conversion to 3 in much improved yields.

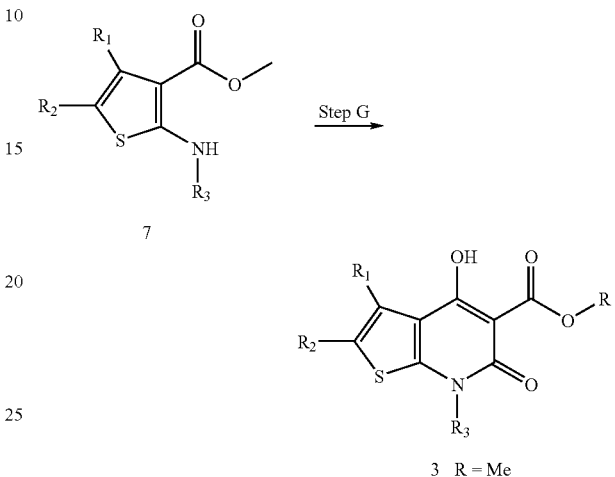

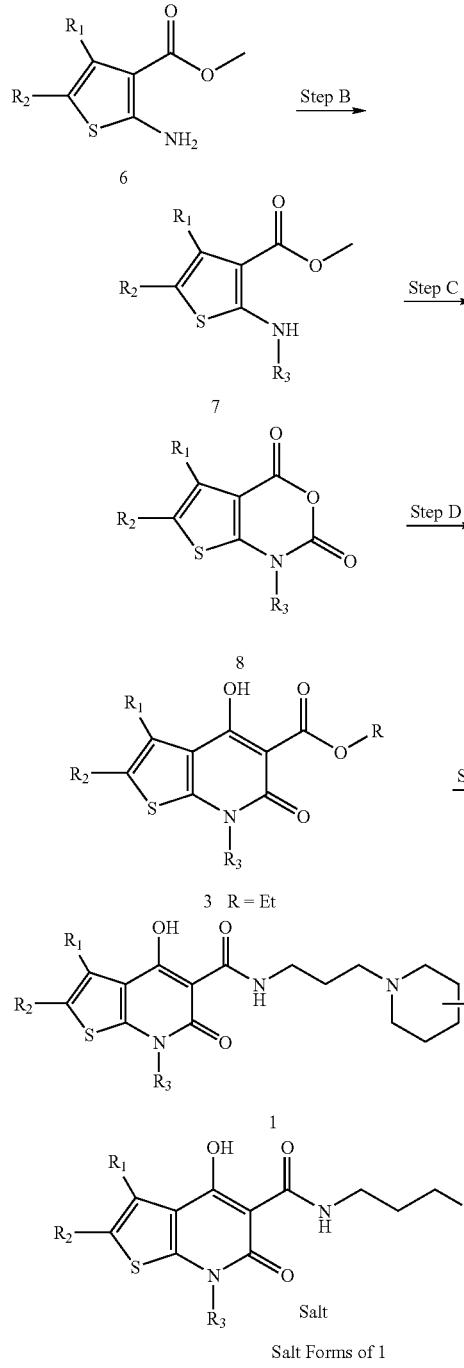

Scheme 4 outlines the preparation of the deoxy derivative 11. In Step H, the ester 3 was first converted to its methanesulfonate derivative, which underwent reductive cleavage with the use of zinc dust and glacial acetic acid at reflux to give the ester 9. Hydrolysis of 9 in Step I followed by amide formation in Step J with 2 afforded the deoxy analog 11 in acceptable yields.

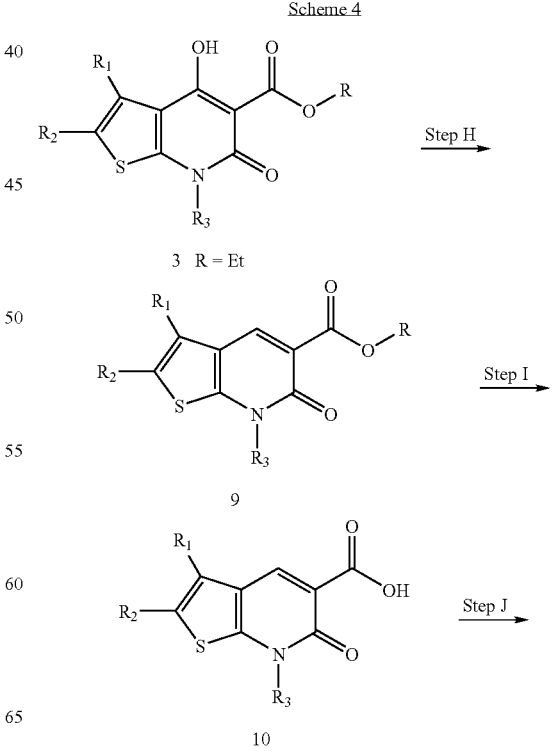

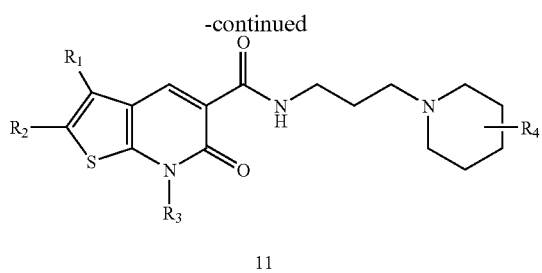

Derivatization of the hydroxyl group of 1 can be effected by Step K in Scheme 5. Treatment of 1 with n-butyllithium at low temperature followed by an electrophile (such as methyl iodide, ethyl chloroformate and pivalic anhydride) resulted in the formation of respective derivatives (methyl ether, ethyl carbonate and pivalate).

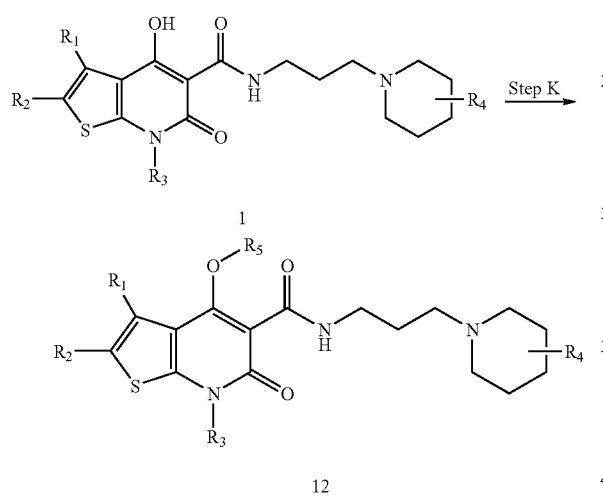

EXAMPLE 1

6,7-Dihydro-4-hydroxy-7-isobutyl-6-oxo-N-(3-(piperidin-1-yl)propyl)thieno[2,3-b]pyridine-5-carboxamide hydrochloride salt Step A: Preparation of 3-(piperidin-1-yl)propan-1-amine A mixture of N-(3-bromopropyl)phthalimide (5.40 g, 20.1 mmol) and piperidine (10 mL) was heated at 80° C.; after 15 min the reaction mixture solidified. This solid was cooled to room temperature, dissolved in water and extracted with ethyl acetate. The extract was washed with water, dried over anhydrous sodium sulfate, filtered and concentrated to yield a slightly yellow viscous oil (4.12 g). To a solution of this oil in ethanol (20 mL) was added hydrazine hydrate (4 mL); the mixture was heated at reflux for 18 h to result in copious amount of solid precipitation. The reaction mixture was cooled to room temperature and ether (50 mL) was added. This suspension was filtered and the filtrate was concentrated to provide the title compound as slightly yellow oil (2.12 g, 74% yield). $^1$H NMR (400 MHz, CDCl$_3$): δ 2.74 (t, 2H), 2.37-2.33 (m, 6H), 1.67-1.55 (m, 6H), 1.43 (m, 2H).

Step B: Preparation of methyl 2-(isobutylamino)thiophene-3-carboxylate

To a solution of methyl 2-aminothiophene-3-carboxylate (2.0 g, 12.7 mmol) in dichloromethane (40 mL) and glacial acetic acid (0.72 mL) were added isobutyraldehyde (0.87 g, 12.1 mmol) and sodium triacetoxyborohydride (4.0 g, 18.9 mmol). The reaction mixture was stirred for 18 h at room temperature and concentrated. The residue was dissolved in ethyl acetate, washed with aqueous sodium bicarbonate solution and with water, dried over anhydrous sodium sulfate and concentrated. The residual oil was purified on a silica gel flash chromatography column eluted with 5% ethyl acetate-hexane to afford the title compound as a slightly yellow oil (2.19 g, 81% yield). $^1$H NMR (400 MHz, CDCl$_3$): δ 7.00 (d, 1H), 6.18 (d, 1H), 3.80 (s, 3H), 3.20 (m, 2H), 1.68 (m, 1H), 1.00 (d, 6H).

Step C: Preparation of 1-isobutyl-1H-thieno[2,3-d][1,3]oxazine-2,4-dione

A mixture of methyl 2-(isobutylamino)thiophene-3-carboxylate (2.1 g, 9.9 mmol), sodium hydroxide (0.39 g, 9.8 mmol), water (20 mL) and methanol (10 mL) was heated at reflux for 2 h and cooled to room temperature. Methanol was removed under reduced pressure; the residue was diluted with dichloromethane (10 mL) and cooled to 0° C. Triphosgene (5.85 g, 19.7 mmol) was added portionwise; the reaction mixture was stirred for 18 h and diluted with dichloromethane. The organic layer was separated, dried over anhydrous sodium sulfate and concentrated to provide the crude product as a light brown solid (2.0 g). This material was used in the next step (Step D) without any purification. $^1$H NMR (400 MHz, CDCl$_3$): δ 7.25 (d, 1H), 6.95 (d, 1H), 3.79 (d, 2H), 2.40-2.36 (m, 1H), 1.02 (d, 6H).

Step D: Preparation of ethyl 6,7-dihydro-4-hydroxy-7-isobutyl-6-oxothieno[2,3-b]pyridine-5-carboxylate To a solution of crude 1-isobutyl-1H-thieno[2,3-d][1,3]oxazine-2,4-dione (2.0 g) in N,N-dimethylacetamide (30 mL) were added diethylmalonate (2.13 g, 13.3 mmol) and sodium hydride (0.32 g, 13.3 mmol). The resulting mixture was heated at 110° C. for 4 h, cooled to room temperature, concentrated to dryness and dissolved in water. This aqueous solution was washed with ethyl acetate, acidified with concentrated hydrochloric acid and followed by extraction with dichloromethane. The extract was dried over anhydrous sodium sulfate and concentrated. The residue was purified on a silica gel flash chromatography column eluted with 10% ethyl acetate-hexane to afford the title compound as a slightly yellow oil (1.95 g, 74% yield for Steps C and D combined). $^1$H NMR (400 MHz, CDCl$_3$): δ 7.32 (d, 1H), 6.90 (d, 1H), 4.49 (q, 2H), 3.90 (d, 2H), 2.49 (m, 1H), 1.46 (t, 3H), 0.98 (d, 6H); MS: m/e 296 (M+H$^+$).

Step E: Preparation of 6,7-dihydro-4-hydroxy-7-isobutyl-6-oxo-N-(3-(piperidin-1-yl)propyl)thieno[2,3-b]pyridine-5-carboxamide A mixture of ethyl 6,7-dihydro-4-hydroxy-7-isobutyl-6-oxothieno[2,3-b]pyridine-5-carboxylate (0.1 g, 0.34 mmol), 3-(piperidin-1-yl)propan-1-amine (96 mg, 0.68 mmol) and toluene (15 mL) was heated at 100° C. for 2 h and cooled to room temperature. Solvent was removed under reduced pressure; the residue was purified on a silica gel flash chromatography column eluted with 3% methanol-dichloromethane to afford the title compound as a colorless oil (0.11 g, 83% yield). $^1$H NMR (400 MHz, CDCl$_3$): δ 10.20 (br s, 1H), 7.38 (d, 1H), 6.95 (d, 1H), 3.92 (d, 2H), 3.49-3.44 (m, 2H), 2.90-2.78 (m, 6H), 2.40 (m, 1H), 2.20-1.38 (m, 8H), 1.00 (d, 6H); MS: m/e 392 (M+H$^+$).

Step F: Preparation of 6,7-dihydro-4-hydroxy-7-isobutyl-6-oxo-N-(3-(piperidin-1-yl)propyl)thieno[2,3-b]pyridine-5-carboxamide hydrochloride salt To a solution of 6,7-dihydro-4-hydroxy-7-isobutyl-6-oxo-N-(3-(piperidin-1-yl)propyl)thieno[2,3-b]pyridine-5-carboxamide (0.11 g, 0.28 mmol) in dichloromethane (0.2 mL) was added hydrogen chloride (0.6 mL, 0.6 mmol, 1.0 M solution in diethyl ether). The reaction mixture became cloudy immediately. Additional amount of diethyl ether was added to cause more solid precipitation. These precipitates were collected by vacuum filtration, washed with ether and dried to give the title compound as an off-white solid (0.11 g, 92% yield). $^1$H NMR (400 MHz, CDCl$_3$): δ 7.39 (d, 1H), 7.11 (d, 1H), 3.96 (d, 2H), 3.60-2.25 (m, 8H), 2.19-1.79 (m, 8H), 0.99 (d, 6H); MS: m/e 392 (M+H$^+$).

EXAMPLE 2

6,7-Dihydro-4-hydroxy-N-(3-(4-methylpiperidin-1-yl)propyl)-6-oxo-7-propylthieno[2,3-b]pyridine-5-carboxamide hydrochloride salt The title compound was synthesized in a similar manner to that outlined for Example 1, except that in Step B isobutyraldehyde was replaced by propionaldehyde and that in Step E 3-(piperidin-1-yl)propan-1-amine was replaced by 3-(4-methylpiperidin-1-yl)propan-1-amine.

Step B: Preparation of methyl 2-(propylamino)thiophene-3-carboxylate $^1$H NMR (400 MHz, CDCl$_3$): δ 7.00 (d, 1H), 6.19 (d, 1H), 3.80 (s, 3H), 3.20 (m, 2H), 1.75 (m, 2H), 1.00 (t, 3H).

Step C: Preparation of 1-propyl-1H-thieno[2,3-d][1,3]oxazine-2,4-dione $^1$H NMR (400 MHz, CDCl$_3$): δ 7.32 (d, 1H), 6.92 (d, 1H), 3.90 (t, 2H), 1.90 (m, 2H), 1.01 (t, 3H).

Step D: Preparation of ethyl 6,7-dihydro-4-hydroxy-6-oxo-7-propylthieno[2,3-b]pyridine-5-carboxylate $^1$H NMR (400 MHz, CDCl$_3$): δ 7.33 (d, 1H), 6.91 (d, 1H), 4.49 (q, 2H), 4.01 (t, 2H), 1.85 (m, 2H), 1.45 (t, 3H), 1.01 (t, 3H); MS: m/e 304 (M+Na$^+$).

Step E: Preparation of 6,7-dihydro-4-hydroxy-N-(3-(4-methylpiperidin-1-yl)propyl)-6-oxo-7-propylthieno[2,3-b]pyridine-5-carboxamide $^1$H NMR (400 MHz, CDCl$_3$): δ 10.20 (br s, 1H), 7.38 (d, 1H), 6.97 (d, 1H), 4.00 (q, 2H), 3.50 (q, 2H), 2.92 (m, 2H), 2.41-2.39 (m, 2H), 1.99-1.20 (m, 9H), 1.01 (t, 3H), 0.90 (d, 3H); MS: m/e 392 (M+H$^+$).

Step F: Preparation of 6,7-dihydro-4-hydroxy-N-(3-(4-methylpiperidin-1-yl)propyl)-6-oxo-7-propylthieno[2,3-b]pyridine-5-carboxamide hydrochloride salt $^1$H NMR (400 MHz, CDCl$_3$): δ 7.39 (d, 1H), 6.98 (d, 1H), 4.05 (m, 2H), 3.60-3.50 (m, 2H), 3.59-3.00 (m, 2H), 2.69-2.59 (m, 2H), 2.30-1.50 (m, 9H), 1.02 (t, 3H), 1.01 (d, 3H); MS: m/e 392 (M+H$^+$).

EXAMPLE 3

6,7-Dihydro-7-ethyl-4-hydroxy-6-oxo-N-(3-(piperidin-1-yl)propyl)thieno[2,3-b]pyridine-5-carboxamide hydrochloride salt The title compound was synthesized in a similar manner to that outlined for Example 1 except that in Step B isobutyraldehyde was replaced by acetaldehyde.

Step B: Preparation of methyl 2-(ethylamino)thiophene-3-carboxylate $^1$H NMR (400 MHz, CDCl$_3$): δ 7.01 (d, 1H), 6.19 (d, 1H), 3.80 (s, 3H), 3.28 (q, 2H), 1.39 (t, 3H).

Step C: Preparation of 1-ethyl-1H-thieno[2,3-d][1,3]oxazine-2,4-dione $^1$H NMR (400 MHz, CDCl$_3$): δ 7.32 (d, 1H), 6.93 (d, 1H), 4.01 (q, 2H), 1.42 (t, 3H).

Step D: Preparation of ethyl 6,7-dihydro-7-ethyl-4-hydroxy-6-oxothieno[2,3-b]pyridine-5-carboxylate $^1$H NMR (400 MHz, CDCl$_3$): δ 7.34 (d, 1H), 6.92 (d, 1H), 4.47 (q, 2H), 4.14 (q, 2H), 1.47 (t, 3H), 1.40 (t, 3H); MS: m/e 290 (M+Na$^+$).

Step E: Preparation of 6,7-dihydro-7-ethyl-4-hydroxy-6-oxo-N-(3-(piperidin-1-yl)propyl)thieno[2,3-b]pyridine-5-carboxamide $^1$H NMR (400 MHz, CDCl$_3$): δ 10.20 (br s, 1H), 7.40 (d, 1H), 6.94 (d, 1H), 4.19 (q, 2H), 3.45 (q, 2H), 2.40-2.29 (m, 6H), 1.90-1.31 (m, 8H), 1.40 (t, 3H); MS: m/e 364 (M+H$^+$).

Step F: Preparation of 6,7-dihydro-7-ethyl-4-hydroxy-6-oxo-N-(3-(piperidin-1-yl)propyl)thieno[2,3-b]pyridine-5-carboxamide hydrochloride salt $^1$H NMR (400 MHz, CDCl$_3$): δ 7.41 (d, 1H), 6.95 (d, 1H), 4.19 (q, 2H), 3.49-3.32 (m, 2H), 2.41-2.31 (m, 6H), 2.00-1.40 (m, 8H), 1.39 (t, 3H); MS: m/e 364 (M+H$^+$).

EXAMPLE 4

6,7-Dihydro-7-ethyl-4-hydroxy-N-(3-(4-methylpiperidin-1-yl)propyl)-6-oxothieno[2,3-b]pyridine-5-carboxamide hydrochloride salt The title compound was synthesized in a similar manner to that outlined for Example 3 except that in Step E 3-(piperidin-1-yl)propan-1-amine was replaced by 3-(4-methylpiperidin-1-yl)propan-1-amine.

Step E: Preparation of 6,7-dihydro-7-ethyl-4-hydroxy-N-(3-(4-methylpiperidin-1-yl)propyl)-6-oxothieno[2,3-b]pyridine-5-carboxamide $^1$H NMR (400 MHz, CDCl$_3$): δ 10.20 (br s, 1H), 7.37 (d, 1H), 6.95 (d, 1H), 4.17 (q, 2H), 3.47 (q, 2H), 2.91 (m, 2H), 2.42 (m, 2H), 1.92-1.20 (m, 9H), 1.39 (t, 3H), 0.92 (d, 3H); MS: m/e 378 (M+H$^+$).

Step F: Preparation of 6,7-dihydro-7-ethyl-4-hydroxy-N-(3-(4-methylpiperidin-1-yl)propyl)-6-oxothieno[2,3-b]pyridine-5-carboxamide hydrochloride salt $^1$H NMR (400 MHz, CDCl$_3$): δ 7.39 (d, 1H), 6.94 (d, 1H), 4.20 (q, 2H), 3.49 (m, 2H), 2.98 (m, 2H), 2.45 (m, 2H), 1.98-1.25 (m, 7H), 1.40 (t, 3H), 1.00 (d, 3H); MS: m/e 378 (M+H$^+$).

EXAMPLE 5

6,7-Dihydro-7-ethyl-N-(3-(4-ethylpiperidin-1-yl)propyl)-4-hydroxy-6-oxothieno[2,3-b]pyridine-5-carboxamide hydrochloride salt The title compound was synthesized in a similar manner to that outlined for Example 3 except that in Step A piperidine was replaced by 4-ethylpiperidine.

Step A: Preparation of 3-(4-ethylpiperidin-1-yl)propan-1-amine $^1$H NMR (400 MHz, CDCl$_3$): δ 2.93-2.89 (m, 2H), 2.73 (t, 2H), 2.37-2.33 (m, 2H), 1.89-1.83 (m, 2H), 1.69-1.61 (m, 4H), 1.27-1.15 (m, 5H), 0.88 (t, 3H); MS: m/e 171 (M+H$^+$).

Step E: Preparation of 6,7-dihydro-7-ethyl-N-(3-(4-ethylpiperidin-1-yl)propyl)-4-hydroxy-6-oxothieno[2,3-b]pyridine-5-carboxamide $^1$H NMR (400 MHz, CDCl$_3$): δ 10.20 (br s, 1H), 7.37 (d, 1H), 6.95 (d, 1H), 4.15 (q, 2H), 3.48 (m, 2H), 3.00 (m, 2H), 2.50 (m, 2H), 2.00-1.20 (m, 9H), 1.39 (t, 3H), 0.89 (t, 3H); MS: m/e 392 (M+H$^+$).

Step F: Preparation of 6,7-dihydro-7-ethyl-N-(3-(4-ethylpiperidin-1-yl)propyl)-4-hydroxy-6-oxothieno[2,3-b]pyridine-5-carboxamide hydrochloride salt $^1$H NMR (400 MHz, CDCl$_3$): δ 7.39 (d, 1H), 6.96 (d, 1H), 4.18 (q, 2H), 3.50 (m, 2H), 3.05 (m, 2H), 2.52 (m, 2H), 2.02-1.24 (m, 9H), 1.41 (t, 3H), 0.95 (t, 3H); MS: m/e 392 (M+H$^+$).

EXAMPLE 6

6,7-Dihydro-4-hydroxy-7-isopropyl-6-oxo-N-(3-(pyrrolidin-1-yl)propyl)thieno-[2,3-b]pyridine-5-carboxamide hydrochloride salt The title compound was synthesized in a similar manner to that outlined for Example 1 except that in Step B isobutyraldehyde was replaced by acetone and that in Step E 3-(piperidin-1-yl)propan-1-amine was replaced by 3-(pyrrolidin-1-yl)propan-1-amine.

Sep B: Preparation of methyl 2-(isopropylamino)thiophene-3-carboxylate $^1$H NMR (400 MHz, CDCl$_3$): δ 7.00 (d, 1H), 6.15 (d, 1H), 3.80 (s, 3H), 3.51 (m, 1H), 1.30 (d, 6H).

Step C: Preparation of 1-isopropyl-1H-thieno[2,3-d][1,3]oxazine-2,4-dione $^1$H NMR (400 MHz, CDCl$_3$): δ 7.29 (d, 1H), 6.98 (d, 1H), 4.45 (m, 1H), 1.61 (d, 6H).

Step D: Preparation of ethyl 6,7-dihydro-4-hydroxy-7-isopropyl-6-oxothieno[2,3-b]pyridine-5-carboxylate $^1$H NMR (400 MHz, CDCl$_3$): δ 7.38 (d, 1H), 6.91 (d, 1H), 4.44 (q, 2H), 1.60 (d, 6H), 1.42 (t, 3H); MS: m/e 282 (M+H$^+$).

Step E: Preparation of 6,7-dihydro-4-hydroxy-7-isopropyl-6-oxo-N-(3-(pyrrolidin-1-yl)propyl)thieno-[2,3-b]pyridine-5-carboxamide $^1$H NMR (400 MHz, CDCl$_3$): δ 10.30 (br s, 1H), 7.40 (d, 1H), 6.96 (d, 1H), 4.10 (br, 1H), 3.50 (q, 2H), 2.65-2.58 (m, 6H), 1.98-1.80 (m, 6H), 1.61 (d, 6H); MS: m/e 364 (M+H$^+$).

Step F: Preparation of 6,7-dihydro-4-hydroxy-7-isopropyl-6-oxo-N-(3-(pyrrolidin-1-yl)propyl)thieno-[2,3-b]pyridine-5-carboxamide hydrochloride salt $^1$H NMR (400 MHz, CDCl$_3$): δ 10.40 (br s, 1H), 7.40 (d, 1H), 6.98 (d, 1H), 3.90 (br, 1H), 3.50 (m, 1H), 2.40-2.15 (m, 4H), 1.97-1.45 (m, 10H), 1.62 (d, 6H); MS: m/e 378 (M+H$^+$).

EXAMPLE 7

6,7-Dihydro-4-hydroxy-7-isopropyl-6-oxo-N-(3-(piperidin-1-yl)propyl)thieno[2,3-b]pyridine-5-carboxamide hydrochloride salt The title compound was synthesized in a similar manner to that outlined for Example 1 except that in Step B isobutyraldehyde was replaced by acetone and that Steps C and D were replaced by Step G.

Step G: Preparation of methyl 6,7-dihydro-4-hydroxy-7-isopropyl-6-oxothieno-[2,3-b]pyridine-5-carboxylate To a solution of methyl 2-(isopropylamino)thiophene-3-carboxylate (3.50 g, 17.6 mmol) in dichloromethane (50 mL) at 0° C. were added triethylamine (5.33 g, 52.8 mmol) followed by ethyl 3-chloro-3-oxopropionate (3.96 g, 26.3 mmol). The reaction mixture was warmed to room temperature, stirred for 2 h, concentrated and dissolved in ethyl acetate. This solution was washed with water, dried over anhydrous sodium sulfate and concentrated to afford a dark red oily residue (3.50 g). To a solution of this residue in methanol (40 mL) at room temperature were added freshly cut pieces of sodium metal (0.77 g, 33.5 mmol) in portions so as to allow for a gentle reflux. After the addition was complete, the reaction mixture was heated at reflux for 18 h, cooled to room temperature and concentrated. The residue was dissolved in water; the resulting solution was washed with dichloromethane, acidified with concentrated hydrochloric acid and extracted with ethyl acetate. The extract was washed with water, dried over anhydrous sodium sulfate and concentrated. The residual solid was recrystallized from ether to afford the title compound as an off-white solid (1.92 g, 41% yield).

$^1$H NMR (400 MHz, CDCl$_3$): □ 13.84 (s, 1H), 7.33 (d, 1H), 6.91 (d, 1H), 4.83 (br, 1H), 4.01 (s, 3H), 1.63 (d, 6H).

Step E: Preparation of 6,7-dihydro-4-hydroxy-7-isopropyl-6-oxo-N-(3-(piperidin-1-yl)propyl)thieno[2,3-b]pyridine-5-carboxamide ¹H NMR (400 MHz, CDCl₃): δ 10.21 (br s, 1H), 7.40 (d, 1H), 6.90 (d, 1H), 3.48 (m, 2H), 2.45 (m, 6H), 1.40-1.90 (m, 8H), 1.41 (d, 6H); MS: m/e 378 (M+H⁺).

Step F: Preparation of 6,7-dihydro-4-hydroxy-7-isopropyl-6-oxo-N-(3-(piperidin-1-yl)propyl)thieno[2,3-b]pyridine-5-carboxamide hydrochloride salt ¹H NMR (400 MHz, CD₃OD): δ 7.40 (d, 1H), 7.20 (d, 1H), 3.60-2.95 (m, 8H), 2.18-1.40 (m, 8H), 1.61 (d, 6H); MS: m/e 378 (M+H⁺).

EXAMPLE 8

6,7-Dihydro-4-hydroxy-7-isopropyl-N-(3-(4-methylpiperidin-1-yl)propyl)-6-oxothieno[2,3-b]pyridine-5-carboxamide hydrochloride salt The title compound was synthesized in a similar manner to that outlined for Example 7 except that in Step E 3-(piperidin-1-yl)propan-1-amine was replaced by 3-(4-methylpiperidin-1-yl)propan-1-amine.

Step E: Preparation of 6,7-dihydro-4-hydroxy-7-isopropyl-N-(3-(4-methylpiperidin-1-yl)propyl)-6-oxothieno[2,3-b]pyridine-5-carboxamide ¹H NMR (400 MHz, CDCl₃): δ 10.26 (br s, 1H), 7.36 (d, 1H), 6.93 (d, 1H), 4.50 (br, 1H), 3.49-3.44 (m, 2H), 2.91 (d, 2H), 2.43 (t, 2H), 1.96-1.81 (m, 4H), 1.64-1.62 (m, 8H), 1.39-1.26 (m, 5H), 0.91 (d, 3H); MS: m/e 392 (M+H⁺).

Step F: Preparation of 6,7-dihydro-4-hydroxy-7-isopropyl-N-(3-(4-methylpiperidin-1-yl)propyl)-6-oxothieno[2,3-b]pyridine-5-carboxamide hydrochloride salt ¹H NMR (400 MHz, CDCl₃): δ 12.16 (br s, 1H), 10.39 (br s, 1H), 7.36 (d, 1H), 6.96 (d, 1H), 4.50 (br, 1H), 3.55-3.47 (m, 4H), 3.06-2.97 (m, 2H), 2.66-2.60 (m, 2H), 2.35-2.25 (m, 2H), 2.10-1.97 (m, 2H), 1.80 (d, 2H), 1.64 (d, 6H), 1.04 (d, 3H); MS: m/e 392 (M+H⁺).

EXAMPLE 9

6,7-Dihydro-4-hydroxy-7-isopropyl-6-oxo-N-(3-(4-(trifluoromethyl)piperidin-1-yl)propyl)thieno[2,3-b]pyridine-5-carboxamide hydrochloride salt The title compound was synthesized in a similar manner to that outlined for Example 7 except that in Step A piperidine was replaced by 4-(trifluoromethyl)piperidine.

Step A: Preparation of 3-(4-(trifluoromethyl)piperidin-1-yl)propan-1-amine

¹H NMR (400 MHz, CDCl₃): δ 3.75-3.69 (m, 2H), 3.04-3.00 (m, 2H), 2.77-2.73 (m, 2H), 2.42-2.38 (m, 2H), 2.02-1.97 (m, 1H), 1.89-1.78 (m, 4H), 1.67-1.60 (m, 2H), 1.27-1.21 (m, 2H).

Step E: Preparation of 6,7-dihydro-4-hydroxy-7-isopropyl-N-(3-(4-(trifluoromethyl)piperidin-1-yl)propyl)-6-oxothieno[2,3-b]pyridine-5-carboxamide ¹H NMR (400 MHz, CDCl₃): δ 10.30 (br s, 1H), 7.37 (d, 1H), 6.94 (d, 1H), 3.48 (dd, 2H), 3.03 (d, 2H), 2.44 (t, 2H), 2.05-1.78 (m, 7H), 1.73-1.63 (m, 2H), 1.63 (d, 6H); MS: m/e 446 (M+H⁺).

Step F: Preparation of 6,7-dihydro-4-hydroxy-7-isopropyl-6-oxo-N-(3-(4-(trifluoromethyl)piperidin-1-yl)propyl)thieno[2,3-b]pyridine-5-carboxamide hydrochloride salt ¹H NMR (400 MHz, CDCl₃): δ 7.35 (d, 1H), 7.21 (d, 1H), 3.71 (d, 2H), 3.55 (t, 2H), 3.04 (t, 2H), 2.60 (br, 1H), 2.21-2.07 (m, 6H), 1.86-1.75 (m, 2H), 1.63 (d, 6H); MS: m/e 446 (M+H⁺).

EXAMPLE 10

6,7-Dihydro-4-hydroxy-7-isopropyl-6-oxo-N-(3-(4-(methoxycarbonyl)piperidin-1-yl)propyl)thieno[2,3-b]pyridine-5-carboxamide hydrochloride salt The title compound was synthesized in a similar manner to that outlined for Example 7 except that a modified procedure of Step A was used in which piperidine was replaced by methyl piperidine-4-carboxylate.

Step A: Preparation of methyl 1-(3-aminopropyl)piperidine-4-carboxylate

¹H NMR (400 MHz, CDCl₃): δ 3.68 (s, 3H), 2.93-2.85 (m, 2H), 2.73 (t, 2H), 2.39-2.35 (m, 2H), 2.32-2.27 (m, 1H), 2.01-1.88 (m, 4H), 1.80-1.60 (m, 4H), 1.34 (br s, 2H); MS: m/e 201 (M+H⁺).

Step E: Preparation of 6,7-dihydro-4-hydroxy-7-isopropyl-N-(3-(4-(methoxycarbonyl)piperidin-1-yl)propyl)-6-oxothieno[2,3-b]pyridine-5-carboxamide ¹H NMR (400 MHz, CDCl₃): δ 10.28 (br s, 1H), 7.35 (d, 1H), 6.94 (d, 1H), 4.50 (br, 1H), 3.67 (s, 3H), 3.50-3.45 (m, 2H), 2.94-2.87 (m, 2H), 2.43 (t, 2H), 2.32-2.26 (m, 1H), 2.04-1.96 (m, 2H), 1.92-1.77 (m, 6H), 1.62 (d, 6H); MS: m/e 436 (M+H⁺).

Step F: Preparation of 6,7-dihydro-4-hydroxy-7-isopropyl-6-oxo-N-(3-(4-(methoxycarbonyl)piperidin-1-yl)propyl)thieno[2,3-b]pyridine-5-carboxamide hydrochloride salt ¹H NMR (400 MHz, CDCl₃): δ 12.42 (br s, 1H), 10.39 (br s, 1H), 7.36 (d, 1H), 6.96 (d, 1H), 4.50 (br, 1H), 3.73-3.45 (m, 7H), 3.05-2.89 (m, 4H), 2.63-2.54 (m, 3H), 2.32-2.20 (m, 4H), 1.64 (d, 6H); MS: m/e 436 (M+H⁺).

EXAMPLE 11

N-(3-(4,4-Difluoropiperidin-1-yl)propyl)-6,7-dihydro-4-hydroxy-7-isopropyl-6-oxothieno[2,3-b]pyridine-5-carboxamide hydrochloride salt The title compound was synthesized in a similar manner to that outlined for Example 7 except that in Step A piperidine was replaced by 4,4-difluoropiperidine.

Step A: Preparation of
3-(4,4-difluoropiperidin-1-yl)propan-1-amine $^1$H NMR (400 MHz, CDCl$_3$): δ 2.76 (t, 2H), 2.56-2.52 (m, 4H), 2.47-2.43 (m, 2H), 2.04-1.94 (m, 6H), 1.67-1.60 (m, 2H).

Step E: Preparation of N-(3-(4,4-difluoropiperidin-1-yl)propyl)-6,7-dihydro-4-hydroxy-7-isopropyl-6-oxothieno[2,3-b]pyridine-5-carboxamide $^1$H NMR (400 MHz, CDCl$_3$): δ 10.36 (br s, 1H), 7.37 (d, 1H), 6.94 (d, 1H), 4.75 (br, 1H), 3.50 (q, 2H), 2.57-2.51 (m, 4H), 2.51 (t, 2H), 2.09-1.99 (m, 4H), 1.85-1.78 (m, 2H), 1.63 (d, 6H); MS: m/e 414 (M+H$^+$).

Step F: Preparation of N-(3-(4,4-difluoropiperidin-1-yl)propyl)-6,7-dihydro-4-hydroxy-7-isopropyl-6-oxothieno[2,3-b]pyridine-5-carboxamide hydrochloride salt $^1$H NMR (400 MHz, CDCl$_3$): δ 13.27 (br s, 1H), 10.42 (br s, 1H), 7.37 (d, 1H), 6.97 (d, 1H), 4.85 (br, 1H), 3.63-3.49 (m, 4H), 3.12-2.90 (m, 6H), 2.32-2.25 (m, 4H), 1.64 (d, 6H); MS: m/e 414 (M+H$^+$).

EXAMPLE 12

6,7-Dihydro-N-(3-(4,4-dimethylpiperidin-1-yl)propyl)-4-hydroxy-7-isopropyl-6-oxothieno[2,3-b]pyridine-5-carboxamide hydrochloride salt The title compound was synthesized in a similar manner to that outlined for Example 7 except that in Step A piperidine was replaced by 4,4-dimethylpiperidine.

Step A: Preparation of
3-(4,4-dimethylpiperidin-1-yl)propan-1-amine $^1$H NMR (400 MHz, CDCl$_3$): δ 2.73 (t, 2H), 2.40-2.37 (m, 6H), 1.68-1.61 (m, 2H), 1.41-1.38 (m, 4H), 0.91 (s, 6H); MS: m/e 171 (M+H$^+$).

Step E: Preparation of 6,7-dihydro-N-(3-(4,4-dimethylpiperidin-1-yl)propyl)-4-hydroxy-7-isopropyl-6-oxothieno[2,3-b]pyridine-5-carboxamide $^1$H NMR (400 MHz, CDCl$_3$): δ 10.26 (br s, 1H), 7.37 (d, 1H), 6.93 (d, 1H), 4.50 (br, 1H), 3.49-3.44 (m, 2H), 2.46-2.40 (m, 6H), 1.87-1.80 (m, 2H), 1.63 (d, 6H), 1.42-1.40 (m, 4H), 0.91 (s, 6H); MS: m/e 406 (M+H$^+$).

Step F: Preparation of 6,7-dihydro-N-(3-(4,4-dimethylpiperidin-1-yl)propyl)-4-hydroxy-7-isopropyl-6-oxothieno[2,3-b]pyridine-5-carboxamide hydrochloride salt $^1$H NMR (400 MHz, CDCl$_3$): δ 12.16 (br s, 1H), 10.39 (br s, 1H), 7.37 (d, 1H), 6.96 (d, 1H), 4.50 (br, 1H), 3.56-3.52 (m, 2H), 3.45-3.40 (m, 2H), 3.09-3.00 (m, 2H), 2.84-2.76 (m, 2H), 2.35-2.15 (m, 4H), 1.63 (d, 6H), 1.52-1.48 (m, 2H), 1.08 (s, 3H), 1.02 (s, 3H); MS: m/e 406 (M+H$^+$).

EXAMPLE 13

6,7-Dihydro-N-(3-((2R,6S)-2,6-dimethylpiperidin-1-yl)propyl)-4-hydroxy-7-isopropyl-6-oxothieno[2,3-b]pyridine-5-carboxamide hydrochloride salt The title compound was synthesized in a similar manner to that outlined for Example 7 except that in Step A piperidine was replaced by (2R,6S)-2,6-dimethylpiperidine.

Step A: Preparation of 3-((2R,6S)-2,6-dimethylpiperidin-1-yl)propan-1-amine $^1$H NMR (400 MHz, CDCl$_3$): δ 3.75-3.71 (m, 2H), 2.82-2.78 (m, 2H), 2.65 (t, 2H), 2.44 (m, 2H), 1.65-1.54 (m, 4H), 1.32-1.23 (m, 4H), 1.12 (d, 6H).

Step E: Preparation of 6,7-dihydro-N-(3-((2R,6S)-2,6-dimethylpiperidin-1-yl)propyl)-4-hydroxy-7-isopropyl-6-oxothieno[2,3-b]pyridine-5-carboxamide $^1$H NMR (400 MHz, CDCl$_3$): δ 7.34 (d, 1H), 7.19 (d, 1H), 3.53 (t, 2H), 2.10-1.94 (m, 6H), 1.84-1.76 (m, 2H), 1.66-1.50 (m, 10H), 1.37 (d, 6H); MS: m/e 406 (M+H$^+$).

Step F: Preparation of 6,7-dihydro-N-(3-((2R,6S)-2,6-dimethylpiperidin-1-yl)propyl)-4-hydroxy-7-isopropyl-6-oxothieno[2,3-b]pyridine-5-carboxamide hydrochloride salt $^1$H NMR (400 MHz, CDCl$_3$): δ 7.34 (d, 1H), 7.19 (d, 1H), 3.53 (t, 2H), 2.10-1.94 (m, 6H), 1.84-1.76 (m, 2H), 1.66-1.50 (m, 10H), 1.37 (d, 6H); MS: m/e 406 (M+H$^+$).

EXAMPLE 14

6,7-Dihydro-2,3-dimethyl-4-hydroxy-7-isopropyl-6-oxo-N-(3-(piperidin-1-yl)propyl)thieno-[2,3-b]pyridine-5-carboxamide hydrochloride salt The title compound was synthesized in a similar manner to that outlined for Example 7 except that in Step B methyl 2-aminothiophene-3-carboxylate was replaced by ethyl 2-amino-4,5-dimethylthiophene-3-carboxylate.

Step B: Preparation of ethyl 4,5-dimethyl-2-isopropylaminothiophene-3-carboxylate $^1$H NMR (400 MHz, CDCl$_3$): δ 4.22 (q, 2H), 3.50 (m, 1H), 2.20 (s, 6H), 1.39 (t, 3H), 1.29 (d, 6H).

Step G: Preparation of methyl 6,7-dihydro-2,3-dimethyl-4-hydroxy-7-isopropyl-6-oxothieno-[2,3-b]pyridine-5-carboxylate $^1$H NMR (400 MHz, CDCl$_3$): δ 4.10 (br, 1H), 4.00 (s, 3H), 2.40 (s, 3H), 2.35 (s, 3H), 1.60 (d, 6H); MS: m/e 318 (M+Na$^+$).

Step E: Preparation of 6,7-dihydro-2,3-dimethyl-4-hydroxy-7-isopropyl-6-oxo-N-(3-(piperidin-1-yl)propyl)thieno[2,3-b]pyridine-5-carboxamide $^1$H NMR (400 MHz, CDCl$_3$): δ 10.40 (br s, 1H), 4.00 (br, 1H), 3.50-3.40 (m, 2H), 2.41-2.39 (m, 6H), 2.42 (s, 3H), 2.33 (s, 3H), 1.85-1.79 (m, 2H), 1.70-1.60 (m, 4H), 1.61 (d, 6H), 1.50-1.40 (m, 2H); MS: m/e 406 (M+H$^+$).

Step F: Preparation of 6,7-dihydro-2,3-dimethyl-4-hydroxy-7-isopropyl-6-oxo-N-(3-(piperidin-1-yl)propyl)thieno[2,3-b]pyridine-5-carboxamide hydrochloride salt $^1$H NMR (400 MHz, CDCl$_3$): δ 12.20 (br s, 1H), 10.59 (br s, 1H), 4.05 (br, 1H), 3.60-3.50 (m, 4H), 3.15-3.10 (m, 2H), 2.70-2.60 (m, 2H), 2.40 (s, 3H), 2.36 (s, 3H), 2.35-2.28 (m, 4H), 1.98-1.80 (m, 4H), 1.60 (d, 6H), 1.48-1.39 (m, 2H); MS: m/e 406 (M+H$^+$).

EXAMPLE 15

6,7-Dihydro-7-isopropyl-6-oxo-N-(3-(piperidin-1-yl)propyl)thieno [2,3-b]pyridine-5-carboxamide hydrochloride salt Step H: Preparation of ethyl 6,7-dihydro-7-isopropyl-6-oxothieno[2,3-b]pyridine-5-carboxylate To a solution of ethyl 6,7-dihydro-4-hydroxy-7-isopropyl-6-oxothieno[2,3-b]pyridine-5-carboxylate (1.41 g, 5.0 mmol) and triethylamine (0.61 g, 6.0 mmol) in dichloromethane (50 mL) was added methanesulfonyl chloride (0.69 g, 6.0 mmol). The reaction mixture was stirred for 1 h, concentrated and dissolved in ethyl acetate; this solution was washed with water, dried over anhydrous sodium sulfate and concentrated to yield a yellow oily residue (1.49 g). A mixture of this residue, zinc dust (0.6 g) and acetic acid (25 mL) was heated at reflux for 2 h, cooled to room temperature and concentrated. The residue was dissolved in ethyl acetate; the resulting solution was washed with aqueous sodium bicarbonate solution, dried over anhydrous sodium sulfate and concentrated to afford the title compound as a light yellow, viscous oil (1.12 g, 85%). $^1$H NMR (400 MHz, CDCl$_3$): δ 8.43 (s, 1H), 7.11 (d, 1H), 6.99 (d, 1H), 4.81 (br, 1H), 4.39 (q, 2H), 1.67 (d, 6H), 1.40 (t, 3H).

Step I: Preparation of 6,7-dihydro-7-isopropyl-6-oxothieno[2,3-b]pyridine-5-carboxylic acid A mixture of ethyl 6,7-dihydro-7-isopropyl-6-oxothieno[2,3-b]pyridine-5-carboxylate (1.12 g, 4.2 mmol), sodium hydroxide (6.3 mL, 2 N solution in water, 12.6 mmol) and methanol (20 mL) was heated at reflux for 18 h, cooled to room temperature and concentrated to remove methanol. The concentrate was diluted with water, cooled to 0° C. and acidified with concentrated hydrochloric acid. The resulting precipitates were collected by vacuum filtration and dried to provide the title compound as an off-white solid (0.81 g, 82% yield). $^1$H NMR (400 MHz, CDCl$_3$): δ 8.86 (s, 1H), 7.25 (d, 1H), 7.16 (d, 1H), 4.87 (br, 1H), 1.73 (d, 6H).

Step J: Preparation of 6,7-dihydro-7-isopropyl-6-oxo-N-(3-(piperidin-1-yl)propyl)thieno[2,3-]pyridine-5-carboxamide hydrochloride salt A mixture of 6,7-dihydro-7-isopropyl-6-oxothieno[2,3-b]pyridine-5-carboxylic acid (0.12 g, 0.5 mmol), 3-(piperidin-1-yl)propan-1-amine (0.07 g, 0.5 mmol), 1-(3-dimethylaminopropyl)-3-ethylcarbodiimide (0.10 g, 0.5 mmol), diisopropylethylamine (0.13 g, 1.0 mmol) and dichloromethane (2 mL) was stirred for 18 h and concentrated. The residue was purified on preparative thin-layer chromatography plates eluted with 15% methanol-dichloromethane to give a yellowish gum (0.03 g). This substance was dissolved in dichloromethane (0.1 mL) and treated with hydrogen chloride (0.1 mL, 1.0 M solution in diethyl ether, 0.1 mmol). The reaction mixture became cloudy; additional amount of diethyl ether was added to cause more solid precipitation. These precipitates were collected by vacuum filtration, washed with ether and dried to give the title compound as an off-white solid (0.03 g, 15% yield). $^1$H NMR (400 MHz, CDCl$_3$): δ9.86 (br s, 1H), 8.85 (s, 1H), 7.19 (d, 1H), 7.04 (d, 1H), 4.95 (br, 1H), 3.50 (q, 2H), 2.50-2.44 (m, 6H), 1.91-1.85 (m, 2H), 1.69 (d, 6H), 1.67-1.60 (m, 4H), 1.45 (m, 2H); MS: m/e 362 (M+H$^+$).

EXAMPLE 16

6,7-Dihydro-7-isopropyl-4-methoxy-6-oxo-N-(3-(piperidin-1-yl)propyl)thieno[2,3-b]pyridine-5-carboxamide Step K: Preparation of 6,7-dihydro-7-isopropyl-4-methoxy-6-oxo-N-(3-(piperidin-1-yl)propyl)thieno [2,3-b]pyridine-5-carboxamide To a solution of 6,7-dihydro-4-hydroxy-7-isopropyl-N-(3-(4-methylpiperidin-1-yl)propyl)-6-oxothieno[2,3-b]pyridine-5-carboxamide (0.075 g, 0.20 mmol) in THF (2.5 mL) at −78° C. was added n-butyllithium (0.087 mL, 2.5 M in hexanes, 0.22 mmol). The reaction mixture was warmed to 0° C. for 30 min and re-cooled to −78° C.; then methyl iodide (0.037 mL, 0.40 mmol) was added. The mixture was warmed to room temperature, stirred for 4 h and concentrated. The residue was dissolved in dichloromethane; the resulting solution was washed with water, dried over anhydrous sodium sulfate and concentrated to afford the title compound as an off-white solid (0.077 g, 99%). $^1$H NMR (400 MHz, CD$_3$OD): δ 7.35 (d, 1H), 7.20 (d, 1H), 3.55 (t, 2H), 3.49-3.45 (m, 2H), 3.40 (t, 4H), 3.09 (s, 3H), 2.17-2.09 (m, 2H), 1.91 (m, 4H), 1.76-1.62 (m, 2H), 1.64 (d, 6H); MS: m/e 392 (M+H$^+$).

EXAMPLE 17

6,7-Dihydro-7-isopropyl-6-oxo-5-(3-(piperidin-1-yl)propylcarbamoyl)thieno[2,3-b]pyridin-4-yl ethyl carbonate The title compound was synthesized in a similar manner to that outlined for Example 16 except that methyl iodide was replaced by ethyl chloroformate.

Step K: Preparation of 6,7-dihydro-7-isopropyl-6-oxo-5-(3-(piperidin-1-yl)propylcarbamoyl)thieno[2,3-b]pyridin-4-yl ethyl carbonate $^1$H NMR (400 MHz, CDCl$_3$): δ 10.20 (br s, 1H), 8.05 (d, 1H), 7.36 (d, 1H), 4.34 (br, 1H), 3.48-3.46 (m, 2H), 3.05-3.00 (m, 8H), 2.65-2.55 (m, 4H), 2.00-1.95 (m, 2H), 1.72-1.33 (m, 11H); MS: m/e 450 (M+H$^+$).

EXAMPLE 18

6,7-Dihydro-7-isopropyl-6-oxo-5-(3-(piperidin-1-yl)propylcarbamoyl)thieno[2,3-b]pyridin-4-yl pivalate The title compound was synthesized in a similar manner to that outlined for Example 16 except that methyl iodide was replaced by pivalic anhydride.

Step K: Preparation of 6,7-dihydro-7-isopropyl-6-oxo-5-(3-(piperidin-1-yl)propylcarbamoyl)thieno[2,3-b]pyridin-4-yl pivalate $^1$H NMR (400 MHz, CDCl$_3$): δ 10.26 (br s, 1H), 7.36 (d, 1H), 6.93 (d, 1H), 4.50 (br, 1H), 3.48-3.43 (m, 2H), 2.52-2.47 (m, 6H), 1.92-1.84 (m, 2H), 1.67-1.59 (m, 10H), 1.48-1.44 (m, 2H), 1.20 (s, 9H); MS: m/e 462 (M+H$^+$).

EXAMPLE 19

6,7-Dihydro-4-hydroxy-7-isopropyl-6-oxo-N-(3-(piperidin-1-yl)propyl)thieno[2,3-b]pyridine-5-carboxamide maleate salt The title compound was synthesized in a similar manner to that outlined for Example 7 except that in Step F hydrogen chloride was replaced by maleic acid.

Step F: Preparation of 6,7-dihydro-4-hydroxy-7-isopropyl-6-oxo-N-(3-(piperidin-1-yl)propyl)thieno[2,3-b]pyridine-5-carboxamide maleate salt $^1$H NMR (400 MHz, CDCl$_3$): δ 11.95 (br s, 1H), 10.40 (br s, 1H), 7.39 (d, 1H), 6.98 (d, 1H), 6.35 (s, 2H), 3.70-3.50 (m, 4H), 3.15-3.08 (m, 2H), 2.70-2.60 (m, 2H), 2.20-1.80 (m, 8H), 1.61 (d, 6H); MS: m/e 378 (M+H$^+$).

EXAMPLE 20

6,7-Dihydro-4-hydroxy-7-isopropyl-6-oxo-N-(3-(piperidin-1-yl)propyl)thieno[2,3-b]pyridine-5-carboxamide citrate salt The title compound was synthesized in a similar manner to that outlined for Example 7 except that in Step F hydrogen chloride was replaced by citric acid.

Step F: Preparation of 6,7-dihydro-4-hydroxy-7-isopropyl-6-oxo-N-(3-(piperidin-1-yl)propyl)thieno[2,3-b]pyridine-5-carboxamide citrate salt $^1$H NMR (400 MHz, CD$_3$OD): δ 7.35 (d, 1H), 7.20 (d, 1H), 3.54 (t, 2H), 3.19-3.15 (m, 3H), 2.11-2.02 (m, 3H), 2.85-2.73 (m, 6H), 1.90-1.80 (m, 4H), 1.76-1.62 (m, 2H), 1.68-1.63 (m, 8H); MS: m/e 378 (M+H$^+$).

EXAMPLE 21

6,7-Dihydro-4-hydroxy-7-isopropyl-6-oxo-N-(3-(piperidin-1-yl)propyl)thieno[2,3-b]pyridine-5-carboxamide succinate salt The title compound was synthesized in a similar manner to that outlined for Example 7 except that in Step F hydrogen chloride was replaced by succinic acid.

Step F: Preparation of 6,7-dihydro-4-hydroxy-7-isopropyl-6-oxo-N-(3-(piperidin-1-yl)propyl)thieno[2,3-b]pyridine-5-carboxamide succinate salt $^1$H NMR (400 MHz, CDCl$_3$): δ 10.36 (br s, 1H), 7.37 (d, 1H), 6.97 (d, 1H), 4.88 (br, 1H), 3.50 (q, 2H), 3.18-2.98 (m, 6H), 2.60 (s, 4H), 2.12-2.05 (m, 2H), 1.92-1.85 (m, 4H), 1.68-1.56 (m, 2H), 1.64 (d, 6H); MS: m/e 378 (M+H$^+$).

EXAMPLE 22

6,7-Dihydro-4-hydroxy-7-isopropyl-6-oxo-N-(3-(piperidin-1-yl)propyl)thieno[2,3-b]pyridine-5-carboxamide sodium salt The title compound was synthesized in a similar manner to that outlined for Example 7 except that in Step F hydrogen chloride was replaced by sodium hydride.

Step F: Preparation of 6,7-dihydro-4-hydroxy-7-isopropyl-6-oxo-N-(3-(piperidin-1-yl)propyl)thieno[2,3-b]pyridine-5-carboxamide sodium salt $^1$H NMR (400 MHz, d$_6$-DMSO): δ 10.72 (br s, 1H), 7.12 (d, 1H), 6.80 (d, 1H), 4.72 (br, 1H), 3.37-3.28 (m, 6H), 3.14 (m, 2H), 2.26 (m, 4H), 1.59-1.34 (m, 10H); MS: m/e 378 (M+H$^+$).

EXAMPLE 23

6,7-Dihydro-4-hydroxy-7-isopropyl-6-oxo-N-(3-(piperidin-1-yl)propyl)thieno[2,3-b]pyridine-5-carboxamide potassium salt The title compound was synthesized in a similar manner to that outlined for Example 7 except that in Step F hydrogen chloride was replaced by potassium tert-butoxide.

Step F: Preparation of 6,7-dihydro-4-hydroxy-7-isopropyl-6-oxo-N-(3-(piperidin-1-yl)propyl)thieno[2,3-b]pyridine-5-carboxamide potassium salt $^1$H NMR (400 MHz, d$_6$-DMSO): δ 10.72 (br s, 1H), 7.12 (d, 1H), 6.80 (d, 1H), 4.72 (br, 1H), 3.37-3.28 (m, 6H), 3.14 (m, 2H), 2.26 (m, 4H), 1.59-1.34 (m, 10H); MS: m/e 378 (M+H$^+$).

Biological Activity of Thienopyridinone Derivatives

Compounds of the invention were synthesized as described above and their binding affinity to 5-HT$_4$, 5-HT$_{4a}$ and 5-HT$_{4e}$ receptors was determined. The biological activity of the novel thienopyridone derivatives is shown in Table 1.

TABLE 1

Biological Activity of novel thienopyridinone derivatives in h 5-HT4e receptor assay

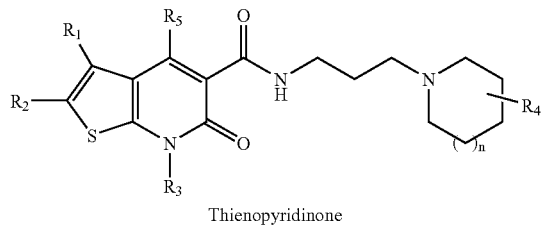

Thienopyridinone

Chemical Structure Activity Data:

| Compound | Chemical Structure | Chemical Name | $K_i$ vs 5-$HT_{4e}$ |
|---|---|---|---|
| 1 | 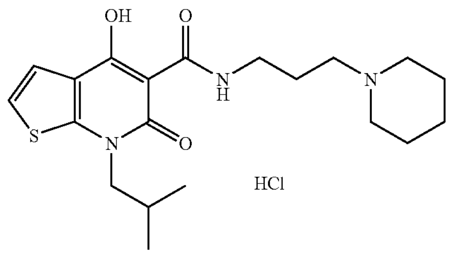 | 6,7-Dihydro-4-hydroxy-7-isobutyl-6-oxo-N-(3-(piperidin-1-yl)propyl)thieno[2,3-b]pyridine-5-carboxamide hydrochloride salt | 120 nM |
| 2 | 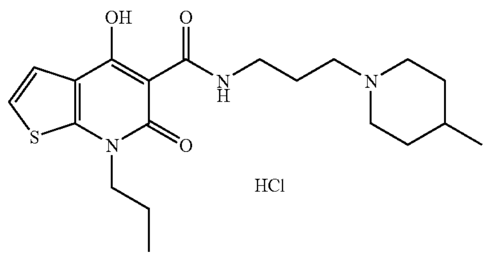 | 6,7-Dihydro-4-hydroxy-N-(3-(4-methylpiperidin-1-yl)propyl)-6-oxo-7-propylthieno[2,3-b]pyridine-5-carboxamide hydrochloride salt | 160 nM |
| 3 | 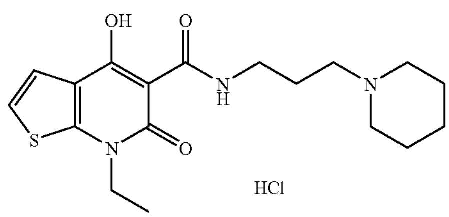 | 6,7-Dihydro-7-ethyl-4-hydroxy-6-oxo-N-(3-(piperidin-1-yl)propyl)thieno[2,3-b]pyridine-5-carboxamide hydrochloride salt | 36 nM |
| 4 | 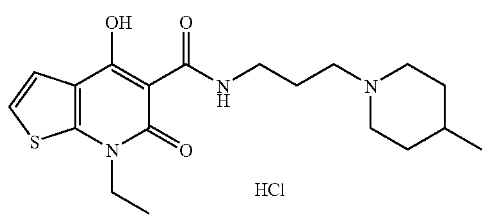 | 6,7-Dihydro-7-ethyl-4-hydroxy-N-(3-(4-methylpiperidin-1-yl)propyl)-6-oxothieno[2,3-b]pyridine-5-carboxamide hydrochloride salt | 20 nM |
| 5 | 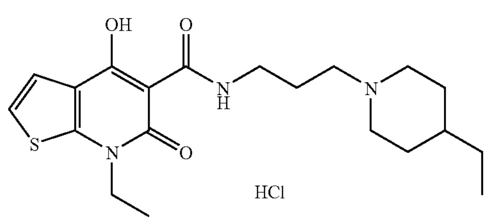 | 6,7-Dihydro-7-ethyl-N-(3-(4-ethylpiperidin-1-yl)propyl)-4-hydroxy-6-oxothieno[2,3-b]pyridine-5-carboxamide hydrochloride salt | 26 nM |

TABLE 1-continued

Biological Activity of novel thienopyridinone derivatives in h 5-HT4e receptor assay

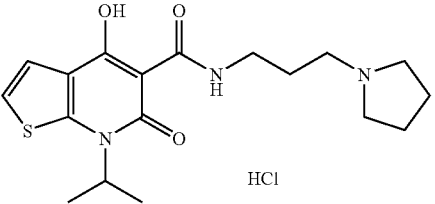

Thienopyridinone

Chemical Structure Activity Data:

| Compound | Chemical Structure | Chemical Name | $K_i$ vs 5-HT$_{4e}$ |
|---|---|---|---|
| 6 | 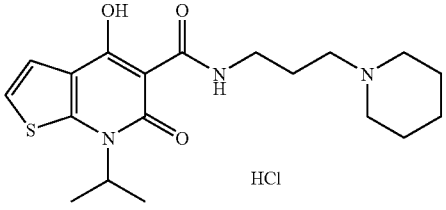 | 6,7-Dihydro-4-hydroxy-7-isopropyl-6-oxo-N-(3-(pyrrolidin-1-yl)propyl)thieno-[2,3-b]pyridine-5-carboxamide hydrochloride salt | 35 nM |
| 7 | 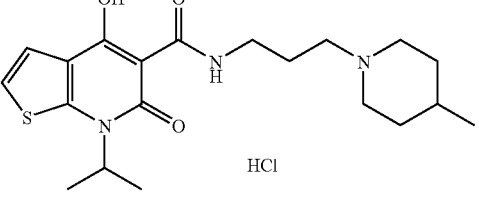 | 6,7-Dihydro-4-hydroxy-7-isopropyl-6-oxo-N-(3-(piperidin-1-yl)propyl)thieno[2,3-b]pyridine-5-carboxamide hydrochloride salt | 21 nM |
| 8 | 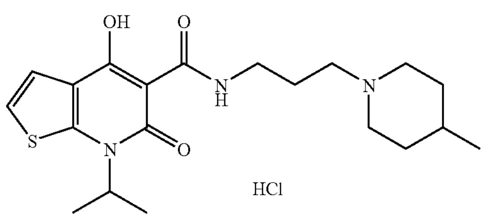 | 6,7-Dihydro-4-hydroxy-7-isopropyl-N-(3-(4-methylpiperidin-1-yl)propyl)-6-oxothieno[2,3-b]pyridine-5-carboxamide hydrochloride salt | 65 nM |
| 9 | 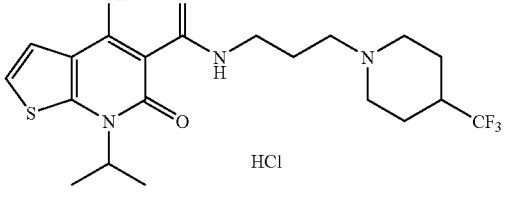 | 6,7-Dihydro-4-hydroxy-7-isopropyl-6-oxo-N-(3-(4-(trifluoromethyl)piperidin-1-yl)propyl)thieno[2,3-b]pyridine-5-carboxamide hydrochloride salt | 50 nM |
| 10 | 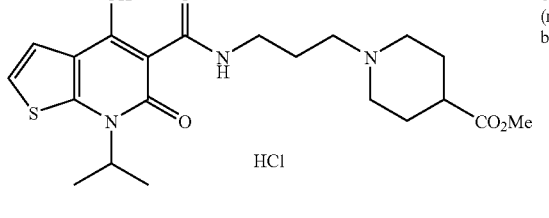 | 6,7-Dihydro-4-hydroxy-7-isopropyl-6-oxo-N-(3-(4-(methoxycarbonyl)piperidin-1-yl)propyl)thieno[2,3-b]pyridine-5-carboxamide hydrochloride salt | 40 nM |

TABLE 1-continued

Biological Activity of novel thienopyridinone derivatives in h 5-HT4e receptor assay

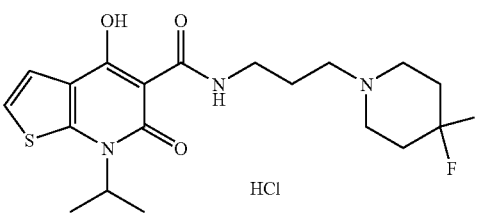

Thienopyridinone

Chemical Structure Activity Data:

| Compound | Chemical Structure | Chemical Name | $K_i$ vs 5-HT$_{4e}$ |
|---|---|---|---|
| 11 | 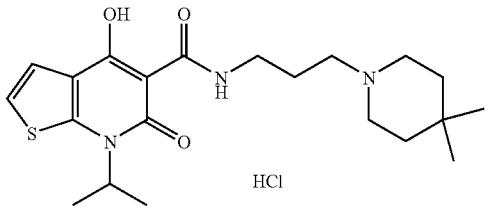 | N-(3-(4,4-Difluoropiperidin-1-yl)propyl)-6,7-dihydro-4-hydroxy-7-isopropyl-6-oxothieno[2,3-b]pyridine-5-carboxamide hydrochloride salt | 220 nM |
| 12 | 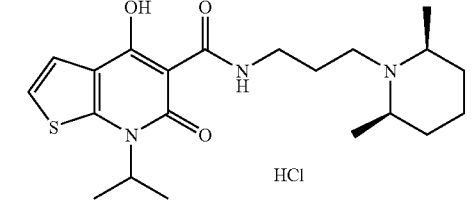 | 6,7-Dihydro-N-(3-(4,4-dimethylpiperidin-1-yl)propyl)-4-hydroxy-7-isopropyl-6-oxothieno[2,3-b]pyridine-5-carboxamide hydrochloride salt | 200 nM |
| 13 | 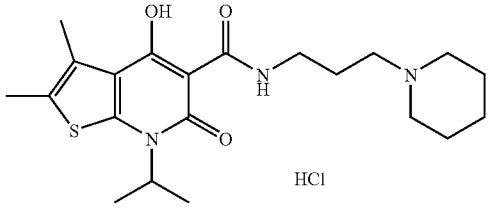 | 6,7-Dihydro-N-(3-((2R,6S)-2,6-dimethylpiperidin-1-yl)propyl)-4-hydroxy-7-isopropyl-6-oxothieno[2,3-b]pyridine-5-carboxamide hydrochloride salt | 380 nM |
| 14 | 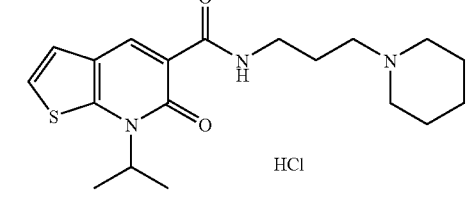 | 6,7-Dihydro-2,3-dimethyl-4-hydroxy-7-isopropyl-6-oxo-N-(3-(piperidin-1-yl)propyl)thieno-[2,3-b]pyridine-5-carboxamide hydrochloride salt | 140 nM |
| 15 | 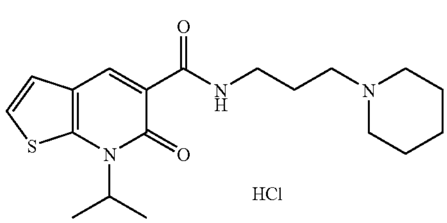 | 6,7-Dihydro-7-isopropyl-6-oxo-N-(3-(piperidin-1-yl)propyl)thieno[2,3-b]pyridine-5-carboxamide hydrochloride salt | 420 nM |

TABLE 1-continued

Biological Activity of novel thienopyridinone derivatives in h 5-HT4e receptor assay Thienopyridinone Chemical Structure Activity Data:

| Compound | Chemical Structure | Chemical Name | $K_i$ vs 5-HT$_{4e}$ |
|---|---|---|---|
| 16 | 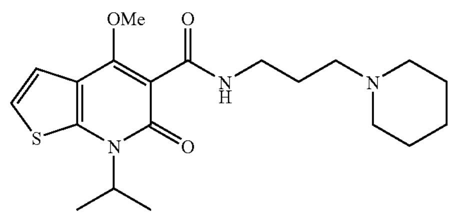 | 6,7-Dihydro-7-isopropyl-4-methoxy-6-oxo-N-(3-(piperidin-1-yl)propyl)thieno[2,3-b]pyridine-5-carboxamide | 31 nM |
| 17 | 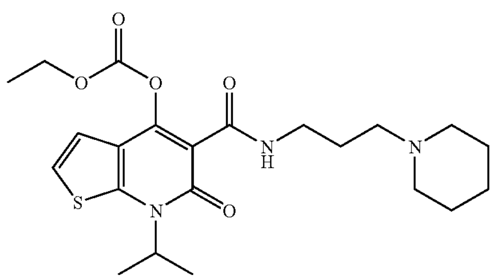 | 6,7-Dihydro-7-isopropyl-6-oxo-5-(3-(piperidin-1-yl)propylcarbamoyl)thieno[2,3-b]pyridin-4-yl ethyl carbonate | Not tested |
| 18 | 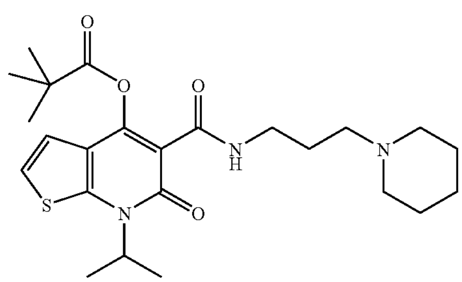 | 6,7-Dihydro-7-isopropyl-6-oxo-5-(3-(piperidin-1-yl)propylcarbamoyl)thieno[2,3-b]pyridin-4-yl pivalate | Not tested |
| 19 | 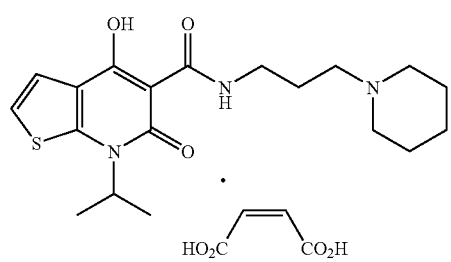 | 6,7-Dihydro-4-hydroxy-7-isopropyl-6-oxo-N-(3-(piperidin-1-yl)propyl)thieno[2,3-b]pyridine-5-carboxamide maleate salt | 37 nM |

TABLE 1-continued

Biological Activity of novel thienopyridinone derivatives in h 5-HT4e receptor assay

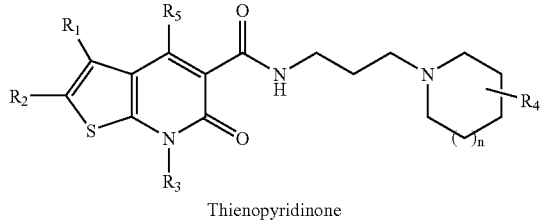

Thienopyridinone

Chemical Structure Activity Data:

| Compound | Chemical Structure | Chemical Name | $K_i$ vs 5-HT$_{4e}$ |
|---|---|---|---|
| 20 | 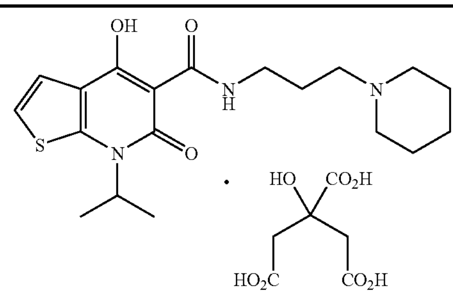 | 6,7-Dihydro-4-hydroxy-7-isopropyl-6-oxo-N-(3-(piperidin-1-yl)propyl)thieno[2,3-b]pyridine-5-carboxamide citrate salt | 53 nM |
| 21 | 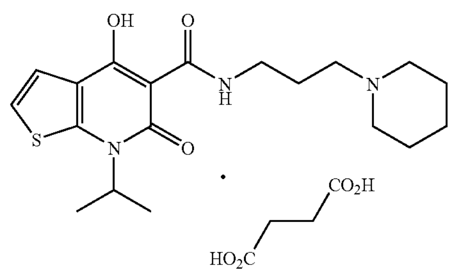 | 6,7-Dihydro-4-hydroxy-7-isopropyl-6-oxo-N-(3-(piperidin-1-yl)propyl)thieno[2,3-b]pyridine-5-carboxamide succinate salt | 31 nM |
| 22 | 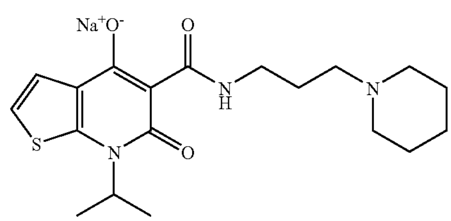 | 6,7-Dihydro-4-hydroxy-7-isopropyl-6-oxo-N-(3-(piperidin-1-yl)propyl)thieno[2,3-b]pyridine-5-carboxamide sodium salt | 140 nM |
| 23 | 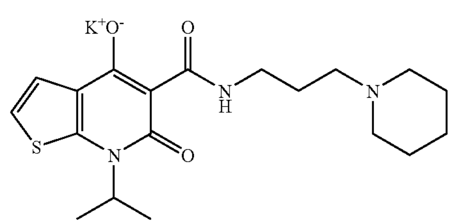 | 6,7-Dihydro-4-hydroxy-7-isopropyl-6-oxo-N-(3-(piperidin-1-yl)propyl)thieno[2,3-b]pyridine-5-carboxamide potassium salt | 27 nM |

Neuroprotective properties of 6,7-Dihydro-4-hydroxy-7-isopropyl-6-oxo-N-(3-(piperidin-2-1-yl)propyl)thieno[2,3-b]pyridine-5-carboxamide potassium salt (compound 23)

Induction of sAPPα Secretion in CHO Cells Transfected with the 5-HT4Re

APP holoprotein is cleaved by α-secretase in the extracellular domain producing a large N-terminal nonamyloidogenic soluble APP (sAPPα), which is secreted in the extracellular medium (Weidemann et al. 1989). Secreted sAPPα has potent neurotrophic and neuroprotective activities. Therefore, elevation of sAPPα levels can have therapeutic benefits in treatments of AD that aim not only to minimize the negative effects of elevated Aβ levels, but also to inhibit the progression of the disease by facilitating the naturally neurotrophic actions of sAPPα fragments. The effect of different concentrations of the hydrochloride salt form of compound 23 on sAPPα release was tested in CHO cells stably expressing the neuronal human 5-HT4Re receptor isoform in 3 different experiments. In this system, the hydrochloride salt form of the active form of compound 23 induced secretion of sAPPα dose dependently with an EC50 value of 4.5-16 nM.

Effect of 6,7-Dihydro-4-hydroxy-7-isopropyl-6-oxo-N-(3-(piperidin-1-yl)propyl)thieno[2,3-b]pyridine-5-carboxamide potassium salt (compound 23), on Memory Performance Reversal of the Scopolamine-Induced Deficit of Water Maze Performance in Rats The Morris Water Maze test is commonly used to study hippocampal-dependent spatial memory acquisition. It consists of a water pool with a hidden escape platform where the rats must learn the location of the platform using either contextual or local cues. The cognitive processes that underlie performance in this test are dependent on many biochemical pathways, most notably the cholinergic system. Lesions of the hippocampus or its cholinergic input impair performance (e.g., by scopolamine) by inducing a performance deficit (latency or time to reach the platform location) in this test without affecting the speed of swimming or other general behaviors in the test animals. Compared with sham injected rats, scopolamine pretreatment (1 mg/kg i.p.) induced a significant acquisition deficit in the water maze task as demonstrated by the ~5-fold increase in latency and path length to find the platform compared with vehicle treated rats. Co-administration of compound 23 at both 15 mg/kg and 30 mg/kg p.o. significantly attenuated the scopolamine-induced deficit as demonstrated by the 25-30% decrease in time and 35-55% decrease in path length to reach the platform.

Effect of compound 23 on Spatial Working Memory in the Spontaneous Alternation Task Performance in Rats Rats have an innate tendency to explore their environment in a systematic way. That is, if a rat chose a certain arm on the first trial in a maze, there is high probability that it will choose a different arm on the second trial. Spontaneous alternation is an ethologically-based test that does not involve reward delivery and represents the tendency to avoid stimulus re-exposure on exploratory behavior. The performance in the spontaneous alternation test is highly dependent on spatial working memory capacity and rats with compromised "working memory" cannot retain information regarding places just visited in memory; therefore they show decreased spontaneous alternation. In this study, rats were tested for spontaneous alternation performance on the cross maze. Rats were allowed to explore the maze freely for 12 minutes. An alternation was recorded if a rat entered all four arms within a series of four consecutive entries. Chance performance is 22.5% with this measure. The compound 23-treated rats (5 mg/kg i.p.) had mean alternation scores significantly higher than those of vehicle-treated rats (58%±3% and 42%±3%, respectively), while the number of arm entries of compound 23 and the vehicle-treated groups did not differ significantly (30%±2% and 26%±3%, respectively). These results suggest that compound 23 enhanced the spatial working memory in the spontaneous alternation task performance in rats.

These novel compounds accordingly are expected to be useful as active and selective 5-HT$_4$ receptor modulators, e.g., in the treatment of a wide variety of clinical conditions including Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, respiratory depression, which are characterized by serotonin excess or absence, e.g., serotoninergic hypofunction or hyperfunction.

EQUIVALENTS

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:
1. A method for making a compound of the formula

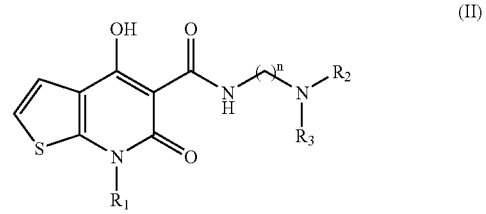

wherein
R$_1$ is (C$_1$-C$_8$) branched or unbranched alkyl;
R$_2$ and R$_3$, taken together, form a substituted or unsubstituted piperidine ring; and
n is 1, 2, 3, 4, 5 or 6;
the method comprising the steps of heating in an organic solvent a mixture comprising a substituted or unsubstituted piperidinyl alkylamine and an intermediate having the formula

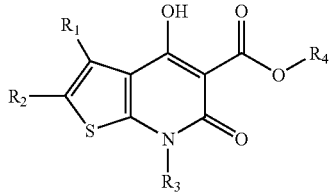
(I)
wherein $R_1$ and $R_2$ are H; and $R_3$ and $R_4$ are independently selected from the group consisting of methyl, ethyl and isopropyl.
2. The method of claim 1, wherein the intermediate is methyl 6,7-dihydro-4-hydroxy-7-isopropyl-6-oxothieno-[2,3-b]pyridine-5-carboxylate.
* * * * *